US011225520B2

(12) United States Patent
Novina et al.

(10) Patent No.: US 11,225,520 B2
(45) Date of Patent: Jan. 18, 2022

(54) IMMUNOTHERAPY COMPOSITIONS AND METHODS

(71) Applicant: DANA-FARBER CANCER INSTITUTE, INC., Boston, MA (US)

(72) Inventors: Carl Novina, Newton, MA (US); Robert Distel, Framingham, MA (US); Alberto Nobili, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/077,939

(22) PCT Filed: Feb. 16, 2017

(86) PCT No.: PCT/US2017/018216
§ 371 (c)(1),
(2) Date: Aug. 14, 2018

(87) PCT Pub. No.: WO2017/143094
PCT Pub. Date: Aug. 24, 2017

(65) Prior Publication Data
US 2019/0256597 A1 Aug. 22, 2019

Related U.S. Application Data

(60) Provisional application No. 62/295,867, filed on Feb. 16, 2016.

(51) Int. Cl.
| C07K 16/32 | (2006.01) |
| C07K 7/08 | (2006.01) |
| A61P 35/00 | (2006.01) |
| A61K 35/17 | (2015.01) |
| C07K 16/28 | (2006.01) |
| A61K 9/00 | (2006.01) |
| C12N 5/0783 | (2010.01) |

(52) U.S. Cl.
CPC ........ *C07K 16/2809* (2013.01); *A61K 9/0019* (2013.01); *A61K 35/17* (2013.01); *A61P 35/00* (2018.01); *C07K 7/08* (2013.01); *C07K 16/32* (2013.01); *C12N 5/0636* (2013.01); *C07K 2317/622* (2013.01); *C07K 2319/03* (2013.01); *C07K 2319/33* (2013.01); *C07K 2319/50* (2013.01)

(58) Field of Classification Search
CPC ...... C07K 16/2809; C07K 7/08; C07K 16/32; A61P 35/00; A61K 35/17; C12N 5/0636
USPC .................................................... 424/135.1
See application file for complete search history.

(56) References Cited

U.S. PATENT DOCUMENTS

| 9,193,791 B2 | 11/2015 | Williams et al. |
| 2013/0060010 A1 | 3/2013 | Avery et al. |
| 2013/0315906 A1 | 11/2013 | Lowman et al. |
| 2015/0238631 A1 | 8/2015 | Kim et al. |
| 2016/0039942 A1 | 2/2016 | Cobbold et al. |
| 2017/0274095 A1 | 9/2017 | Meyer et al. |
| 2018/0104354 A1 | 4/2018 | Kim et al. |

FOREIGN PATENT DOCUMENTS

| CN | 103906760 A | 7/2014 |
| CN | 104321081 A | 1/2015 |
| CN | 104540518 A | 4/2015 |
| CN | 108490174 A | 9/2018 |
| CN | 108660113 A | 10/2018 |
| JP | 2014-504294 A | 2/2014 |
| JP | 2015-509952 A | 4/2015 |
| WO | 2012069089 A1 | 5/2012 |
| WO | WO2012082841 A2 | 6/2012 |
| WO | 2013/128194 A1 | 9/2013 |
| WO | 2013163631 A2 | 10/2013 |
| WO | WO2014100615 A1 | 6/2014 |
| WO | WO2015057852 A1 | 4/2015 |
| WO | 2015116933 A2 | 8/2015 |
| WO | WO2016056228 A1 | 4/2016 |
| WO | WO2016154621 A1 | 9/2016 |
| WO | WO2016168766 A1 | 10/2016 |
| WO | WO2016168769 A1 | 10/2016 |
| WO | WO2017112877 A1 | 6/2017 |
| WO | WO2017133222 A1 | 8/2017 |
| WO | WO2017177149 A2 | 10/2017 |
| WO | WO2018075807 A1 | 4/2018 |
| WO | WO2018152451 A1 | 8/2018 |
| WO | WO2018160622 A1 | 9/2018 |

OTHER PUBLICATIONS

Bremer et al., "In Vivo Molecular Target Assessment of Matrix Metalloproteinase Inhibition," Nature Medicine, Nature Pub. Co., vol. 7, No. 6, Jun. 1, 2001, pp. 743-748, XP001164274.
Donaldson, et al., "Design and development of masked therapeutic antibodies to limit off-target effects: application to anti-EGFR antibodies," Cancer Biology & Therapy, Landes Bioscience, US, vol. 8, No. 22, Nov. 1, 2009, pp. 2147-2152, XP009135774.
Dai, et al., "Chimeric Antigen Receptors Modified T-Cells for Cancer Therapy,"Journal of the National Cancer Institute, vol. 108, No. 7, Jan. 27, 2016, XP055372001.
Choi, et al., "Protease-Activated Drug Development," Theranostics, vol. 2, No. 2, Jan. 1, 2012, pp. 156-179, XP055263145.
Polu, et al., "Probody therapeutics for targeting antibodies to diseased tissue," Expert Opinion on Biological Therapy, vol. 14, No. 8, Aug. 1, 2014, pp. 1049-1053, XP055228738.
Cao, Yu, et al., "Design of Switchable Chimeric Antigen Receptor T Cells Targeting Breast Cancer", Agnew. Chem. Int. Ed. 2016, 55, pp. 1-6.
Changwei, Wang, et al. "MEDI 223: Design, synthesis and Preclinical Study of Novel Taxoid-Based Small Molecule Drug Conjugates (SMDCs) Using Folate/Dimethyltetrahydrofolate (DMTHF) as Tumor Targeting Module", 253rd ACS National Meeting / 2017, Session: Poster.
Chu, Wenqu, et al. "Bi-Specific Ligand-Controlled Chimeric Antigen Receptor T-Cell Therapy for Non-Small Cell Lung Cancer", BioScience Trends. 2018, 12(3), pp. 298-308.

(Continued)

*Primary Examiner* — Yan Xiao
(74) *Attorney, Agent, or Firm* — Burns & Levinson, LLP; Daniel W. Clarke

(57) ABSTRACT

The present invention provides universal immunotherapy compositions useful for targeted treatment of cancers and other immune disorders.

12 Claims, 13 Drawing Sheets

Specification includes a Sequence Listing.

(56) References Cited

OTHER PUBLICATIONS

Kim, Min Soo, et al., "Redirection of Genetically Engineered CART-T Cells Using Bifunctional Small Molecules", Journal of the American Chemical Society 2015, 137, pp. 2832-2835.

Ma, Jennifer S. Y., et al., "Versatile Strategy for Controlling the Specificity and Activity of Engineered T Cells", PNAS, Published online Jan. 12, 2016, pp. E450-E458.

Raj, Deepak, et al., "Switchable CAR-T Cells Mediate Remission in Metastatic Pancreatic Ductal Adenocarcinoma", BMJ, 2018, pp. 1-13.

Tamada, Koji, et al., "Redirecting Gene-Modified T Cells Toward Various Cancer Types Using Tagged Antibodies", American Association for Cancer Research, Dec. 1, 2012.

Zhang, Erhao, et al., "Accurate Control of Dual-Receptor-Engineered T Cell Activity Through a Bifunctional Anti-Angiogenic Peptide", Journal of Hematology & Oncology, 2018.

Figure 1. Protease-specific unmasking strategy to induce tumor-specific T cell responses.

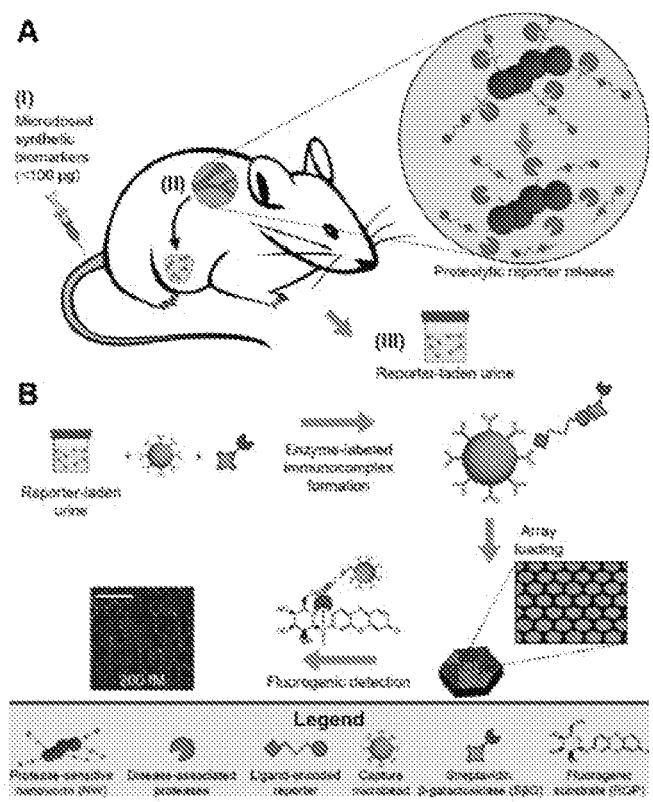

Figure 1. (A) Injected synthetic biomarkers (I) release reporters upon interaction with disease-associated proteases (II). Ligand-encoded reporters liberated from carrier nanoparticles are small enough to be concentrated into the urine (III). (B) The SiMoA assay uses capture antibody-coated beads and S$\beta$G to form reporter–sandwich complexes. Beads are loaded into arrays of ~50,000 wells and sealed with fluorogenic substrate RGP to detect single sandwich complexes. Scale is 50 $\mu$m.

Figure 4

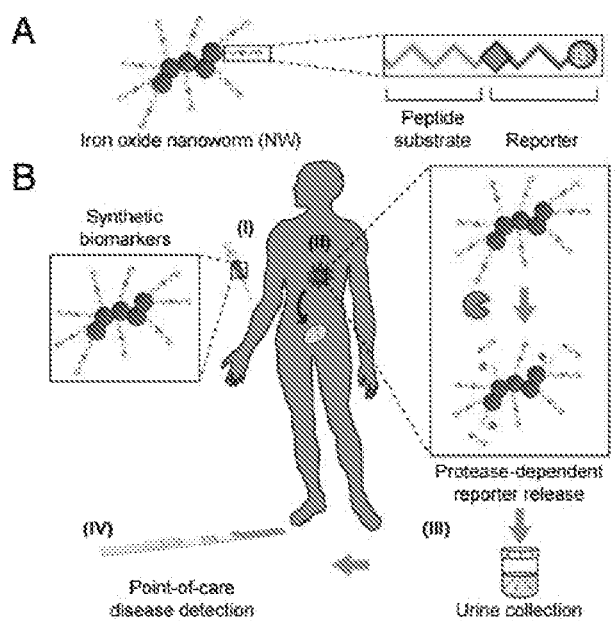

Fig. 1. Protease-sensitive NPs for POC urinary monitoring of disease. (A) Synthetic biomarkers were synthesized by conjugating substrate-reporter tandem peptides to carrier iron oxide NWs. Proteolytic cleavage of the linking peptide substrate liberates ligand-encoded reporters that filter into urine. (B) (I) A patient suspected of harboring a disease receives a disease-tuned diagnostic nanoworm (NW) mixture. (II) NWs infiltrate the disease site and release reporters upon proteolytic cleavage of peptide substrates. Although intact NWs are too large to pass the glomerular basement membrane, liberated reporters passively filter through the kidney. (III) The patient collects a urine sample. (IV) Application of unprocessed urine to a low-cost POC paper lateral flow assay (LFA) enables diagnosis.

Figure 5

Figure 7
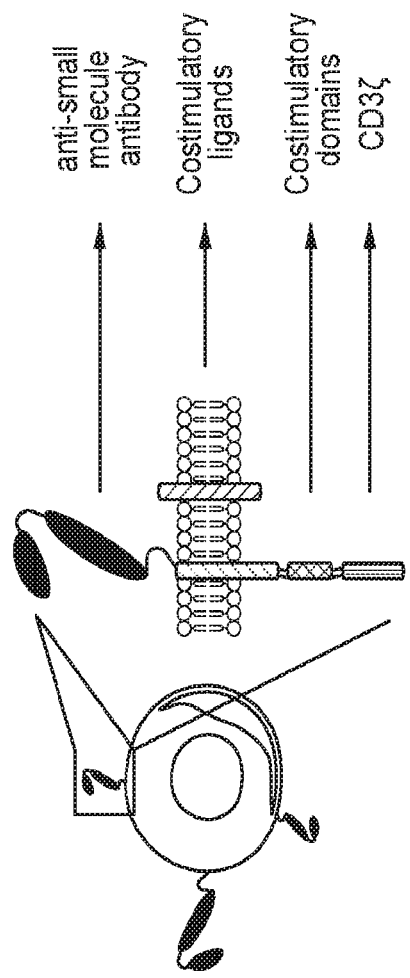
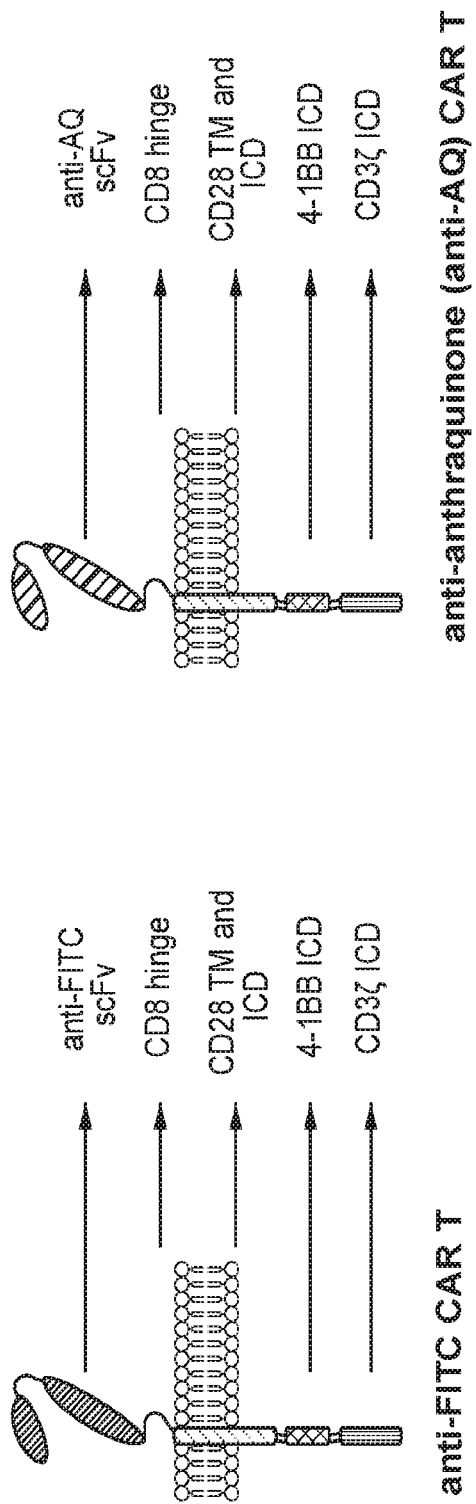

Figure 8
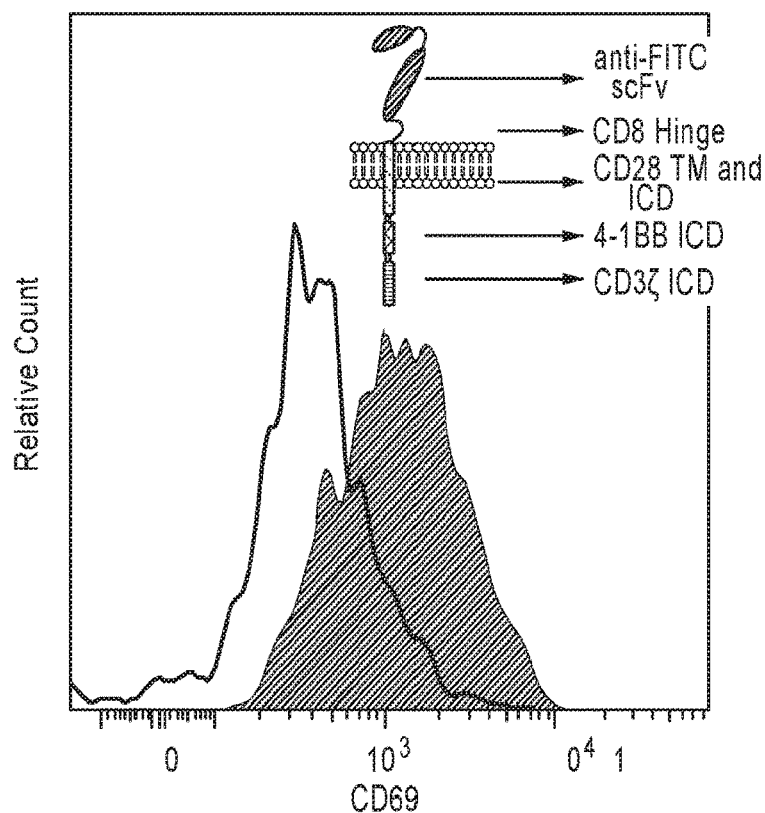
anti-FITC BAT-CAR activation (CD69 upregulation) upon stimulation with BSA-FITC
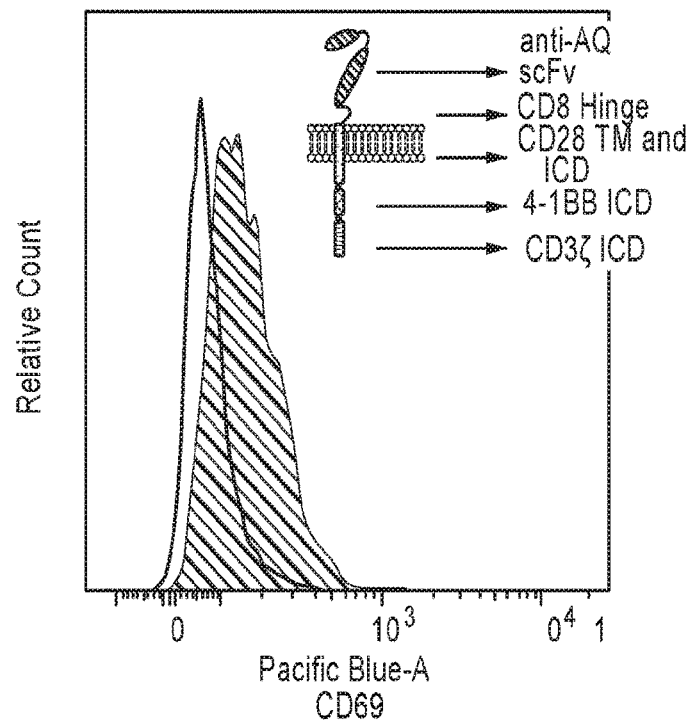
anti-AQ BAT-CAR activation (CD69 upregulation) upon stimulation with pCP(AQ)

FIGURE 10.
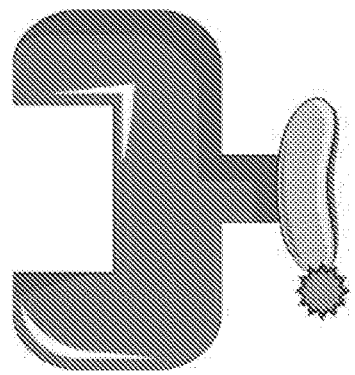
A) TTU+CU*FITC
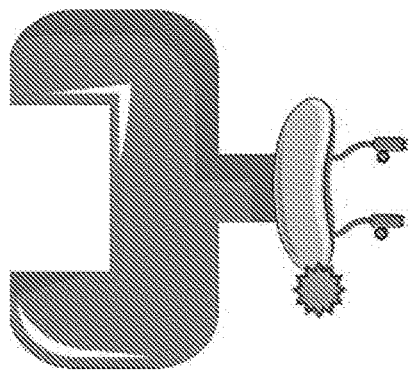
B) TTU+CU*FITC-PEG2-pCP(AQ)
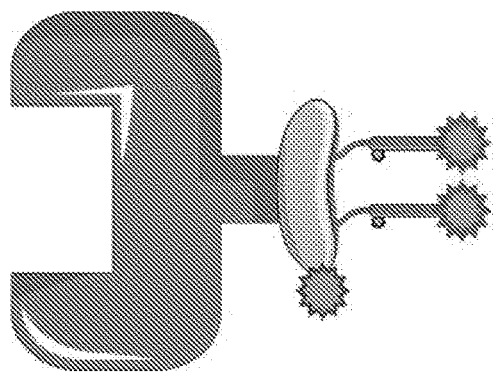
C) TTU+CU*FITC-PEG2-CP(AQ)*A647
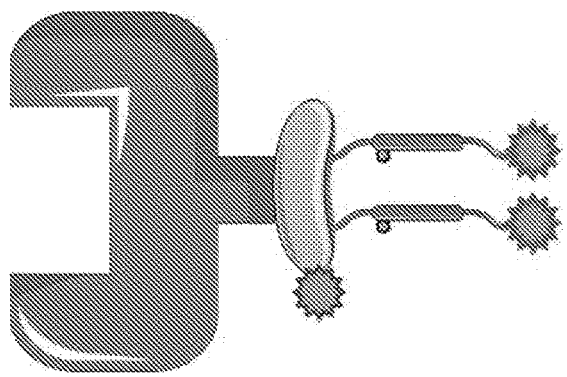
D) TTU+CU*FITC-PEG2-CP(AQ)-PEG12*A647
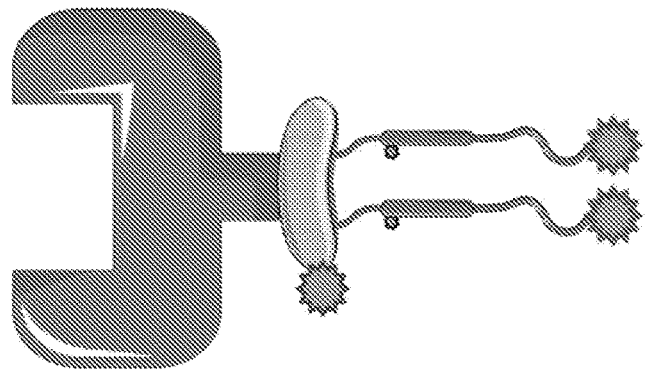
E) TTU+CU*FITC-PEG2-CP(AQ)-PEG24*A647

Figure 12
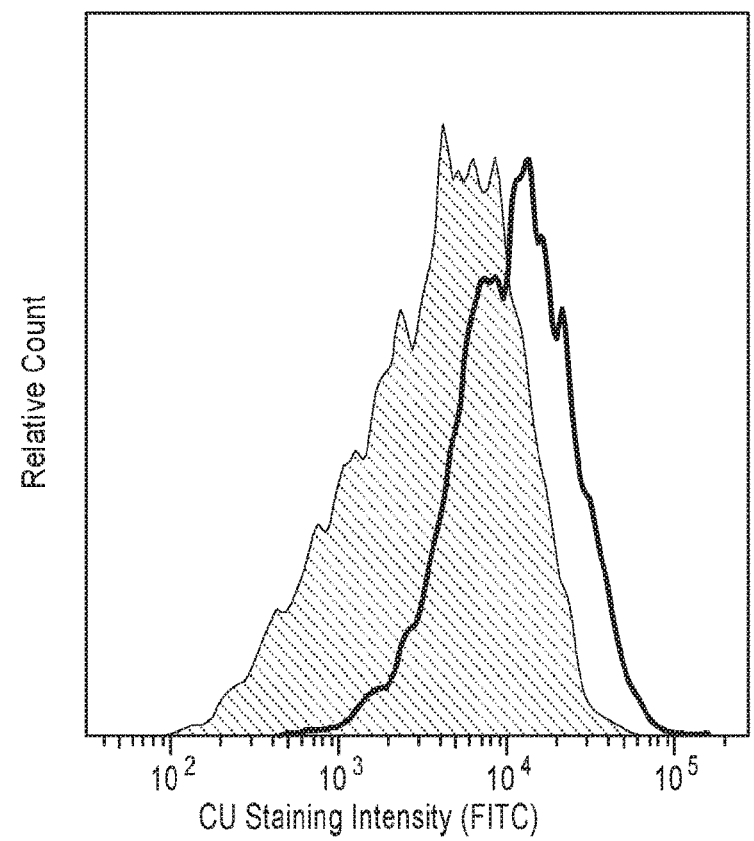
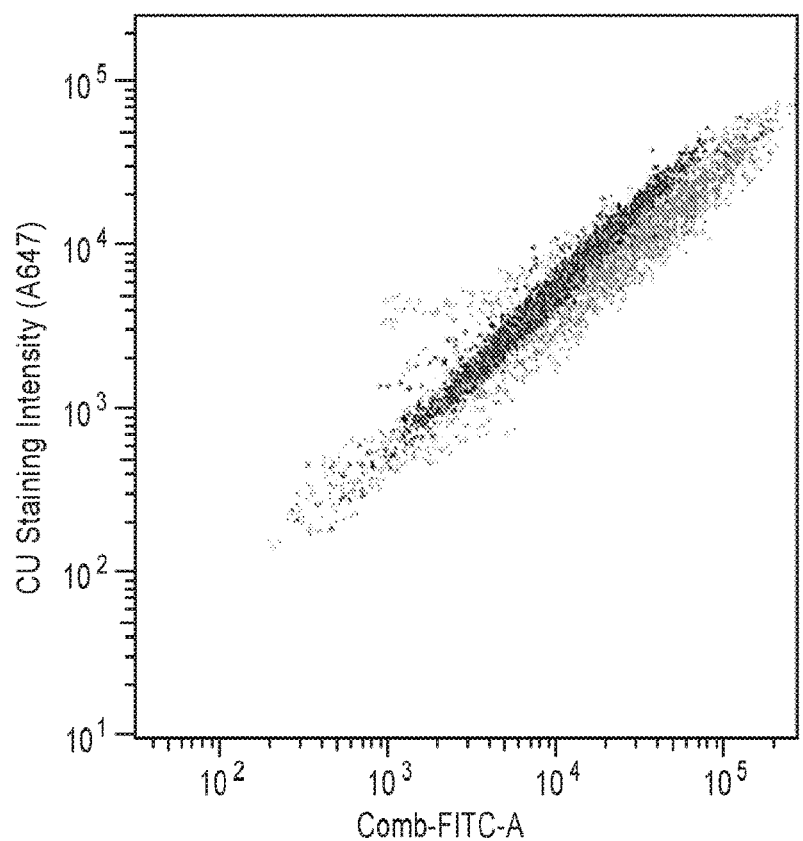

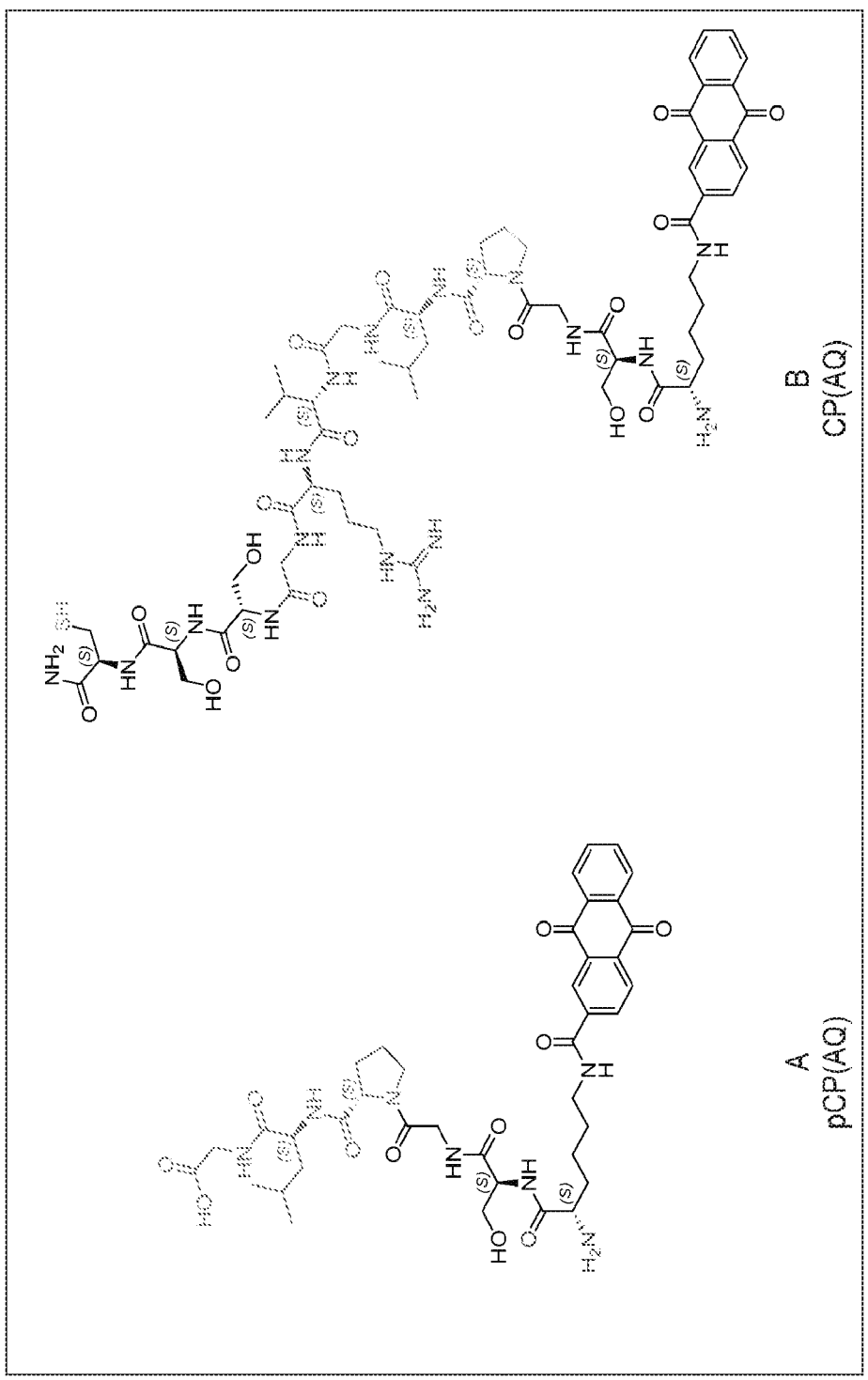
FIGURE 13A. Post-cleavage peptide bond to anthraquinone-2-acid, pCP(AQ): Lys(AQ)SerGlyProLeuGly (SEQ ID NO:1)
FIGURE 13B. Cleavable peptide bond to anthraquinone-2-acid, CP(AQ): Lys(AQ)SerGlyProLeuGlyValArgGlySerSerCys (SEQ ID NO:2)

IMMUNOTHERAPY COMPOSITIONS AND METHODS

RELATED APPLICATIONS

This application is a national stage application, filed under 35 U.S.C. § 371, of International Application No. PCT/US2017/018216, filed Feb. 16, 2017, which claims priority under 35 U.S.C. § 119(e) to, and the benefit of, U.S. Provisional Application No. 62/295,867, filed on Feb. 16, 2016, each of which is incorporated herein by reference in its entirety.

GOVERNMENT INTEREST

This invention was made with government support under grant numbers R01 CA185151 and DK105602 awarded by the National Institutes of Health. The government has certain rights in the invention.

INCORPORATION BY REFERENCE OF SEQUENCE LISTING

The contents of the text file named "52095-556N01US_ST25.txt," which was created on Apr. 25, 2019 and is 14 KB in size, are hereby incorporated by reference in their entirety.

FIELD OF THE INVENTION

The present invention relates generally to universal immunotherapy compositions useful for targeted treatment of cancers and other immune disorders.

BACKGROUND OF THE INVENTION

Clinical trials have demonstrated that cancer immunotherapies can induce durable responses in patients with advanced cancers. One of the most successful cancer immunotherapies is the use of chimeric antigen receptor (CAR) T cells to treat B cell-derived leukemias and lymphomas. The chimera used against these cancers is a single chain antibody specific for CD19 fused to CD28 (a T cell co-stimulatory protein) and then fused to CD3zeta (T cell receptor (TCR) signaling protein). T cells expressing this construct receive primary and secondary signals and generate robust immune responses against all cells expressing CD19—including normal B cells. To date, CAR T cell therapies have demonstrated only modest success against solid tumors in part because it is very difficult to identify antigens that are uniquely expressed on tumors but not on untransformed cells. Even if we could solely target tumor antigens, the vast majority of mutations are private and unique to each patient. Thus, it would be difficult and costly to generate a TCR or antibody that recognizes tumor neoantigens for each patient. The current invention solves this problem.

SUMMARY OF THE INVENTION

In various aspects the invention provides a binding molecule having specificity for a tumor antigen wherein the binding molecule includes a recognition domain linked to a protection domain. The recognition domain specifically binds to a secondary binding molecule. In some aspects the secondary binding molecule is on a cell. The cell is for example, a chimeric antigen receptor T cell (CART), a T-lymphocyte, a B-lymphocyte or natural killer cell. The binding molecule is an antibody, an affimer, an aptamer or a T-cell receptor (TCR) multimer The antibody is aFab or a scFV. The TCR multimer is a tetramer In some aspects the protection domain includes a carrier domain linked to a protease susceptible peptide. The protease susceptible peptide is specific for a tumor protease. Alternatively the protection domain is pH sensitive. The recognition domain is linked to the protection domain such that the recognition domain is masked such that when the protection domain is contacted with a protease or a specific pH the recognition domain is unmasked.

The carrier domain is a polymer such as for example PEG-diacrylate.

The recognition domain is a small molecule. In some aspects the recognition domain is a multimer. For example, the recognition domain is a naturally-occurring inorganic or organic compound, an inorganic or organic synthetic compound, a biological molecule. The biological molecule is a drug, a toxin, a hormone, a metal, a cytokine, a peptide or a nucleic acid. Exemplary recognition domains include an amphetamine, a benzodiazepine, a benzoylecgonine, a buprenorphine, an opioid, a cannabinoid, a phencyclidine a tricyclic antidepressant, dextromethorphan, fentanyl, meprobamate, methadone, methamphetamine, oxycodone, THC, tramadol, zolpidem, ketamine, LSD, MDMA, methaqualone, propoxyphene or norketimine.

In other aspect the invention provides a chimeric antigen receptor (CAR) comprising an intracellular signaling domain, a transmembrane domain and an extracellular domain capable of specifically binding a recognition domain. The extracellular domain is an antibody such as a Fab or a scFV. The transmembrane domain further includes a stalk region positioned between the extracellular domain and the transmembrane domain. The transmembrane domain includes CD28.

The CAR further includes one or more additional costimulatory molecules positioned between the transmembrane domain and the intracellular signaling domain. The costimulatory molecule is for example, CD28, 4-1BB, 4-1BBL ICOS, or OX40.

In various aspects the intracellular signaling domain comprises a CD3 zeta chain.

Also provided is a nucleic acid encoding the CAR according to the invention, vectors including the nucleic acid and cells containing the vector. The cell is a T cell such as for example, a CD4$^+$ T-cell and/or CD8$^+$ T-cell a T regulatory cell (Treg) or a T follicular regulatory cell (TFR).

In other aspects the invention provides a genetically engineered cell which expresses and bears on the cell surface membrane the chimeric antigen receptor according to the invention. The cell is a T cell such as for example, a CD4$^+$ T-cell and/or CD8$^+$ T-cell a T regulatory cell (Treg) or a T follicular regulatory cell (TFR).

In other aspects the invention provides a pharmaceutical composition containing the population of the genetically engineered cells according to the invention.

In yet another aspect the invention provides a system including a binding molecule having specificity for a tumor antigen wherein the binding molecule has a recognition domain linked to protection domain and a chimeric antigen receptor (CAR) having an intracellular signaling domain, a transmembrane domain and an extracellular domain capable of specifically binding the recognition domain. In some aspects the CAR is expressed on a cell. The cell is a T cell such as for example, a CD4$^+$ T-cell and/or CD8$^+$ T-cell a T regulatory cell (Treg) or a T follicular regulatory cell (TFR).

In a further aspect the invention provides a system including a binding molecule having specificity for a tumor antigen wherein the binding molecule comprises (i) a cleavable masking moiety that inhibits the binding of the binding moiety to the tumor antigen and (ii) a recognition domain; and a chimeric antigen receptor (CAR) having an intracellular signaling domain, a transmembrane domain and an extracellular domain capable of specifically binding the recognition domain.

The binding molecule is an antibody, an affimer, an aptamer or a T-cell receptor (TCR) multimer The antibody is aFab or a scFV, The TCR multimer is a tetramer The cleavable masking moiety is a protease susceptible peptide.

In yet other aspects the invention provides methods of treating cancer in a subject in need thereof by administering to the subject a binding molecule according to the invention at a first period of time and a CAR according to the invention at a second period of time.

In another aspect the invention provides methods of treating cancer in a subject in need thereof by administering to the subject at a first period of time a binding molecule having specificity for a tumor antigen wherein the binding molecule has (i) a cleavable masking moiety that inhibits the binding of the binding moiety to the tumor antigen and (ii) a recognition domain; and administering to the subject at a second period of time a chimeric antigen receptor (CAR) comprising an intracellular signaling domain, a transmembrane domain and an extracellular domain capable of specifically binding the recognition domain.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 4. Illustrates an assay to define protease secretion of tumors.

FIG. 5. Illustrates an assay to define protease secretion of tumors.

FIG. 6 as FIGS. 7, 8 and 10 were generated using the figure templates freely available at http://www.servier.com/Powerpoint-image-bank.

FIG. 7. Schematic presentation of a BAT-CAR T cell and examples of CAR modules used in the present patent.

FIG. 8. Activation of a population of 58 C cells transduced with either anti-FITC or anti-AQ CAR modules. FACS analysis, CD69 over-expression as readout.

FIG. 10. Schematic presentation of the different CU/TTU combinations used to verify CU binding to TTU.

FIG. 12. Top. HER2+ cell staining with CU*FITC-PEG2-C(AQ)-PEG24*A647±unlabelled TTU. FACS analysis, FITC readout. Bottom. Comparison of signal intensity of two different populations of HER2+ cells stained with the same CU*FITC-PEG2-C(AQ)-PEG24*A647+ unlabelled TTU over time. FACS analysis, FITC signal as readout, two time points: 30 minutes incubation on ice (red), 8 hours incubation at 37° C./5% CO2.

FIG. 13. Sequences of peptides carrying anthraquinone (AQ) small molecule. Post-cleavage peptide (pCP(AQ)) and cleavable peptide (CP(AQ)).

DETAILED DESCRIPTION OF THE INVENTION

The present invention relates to a universal immunotherapy systems, compositions and methods of treating cancer and other immunological disorders such as autoimmune disease and graft vs host disease.

One of the biggest impediments to cancer immunotherapy is identifying antigens uniquely expressed on tumor tissue but not expressed on normal, healthy tissue. The present invention overcomes these challenges by leveraging several technological innovations to create an effective and universal CAR T cell therapy system. Specifically, the present invention provides systems reagents that allow detection of any antigen on a tumor and generation of immune reactivity against that tumor without off-target tissue effects.

Briefly, the in various aspects the current invention is composed of three essential parts (1) a tumor-targeting binding molecule. (2) a masked small molecule, and (3) a CAR T cell specific for the small molecule. The mask is sensitive to biological molecules secreted by the tumor (e.g., proteases, lipases, glyosidases) or pH that results in "unmasking" of the small molecule.

Figure 1:
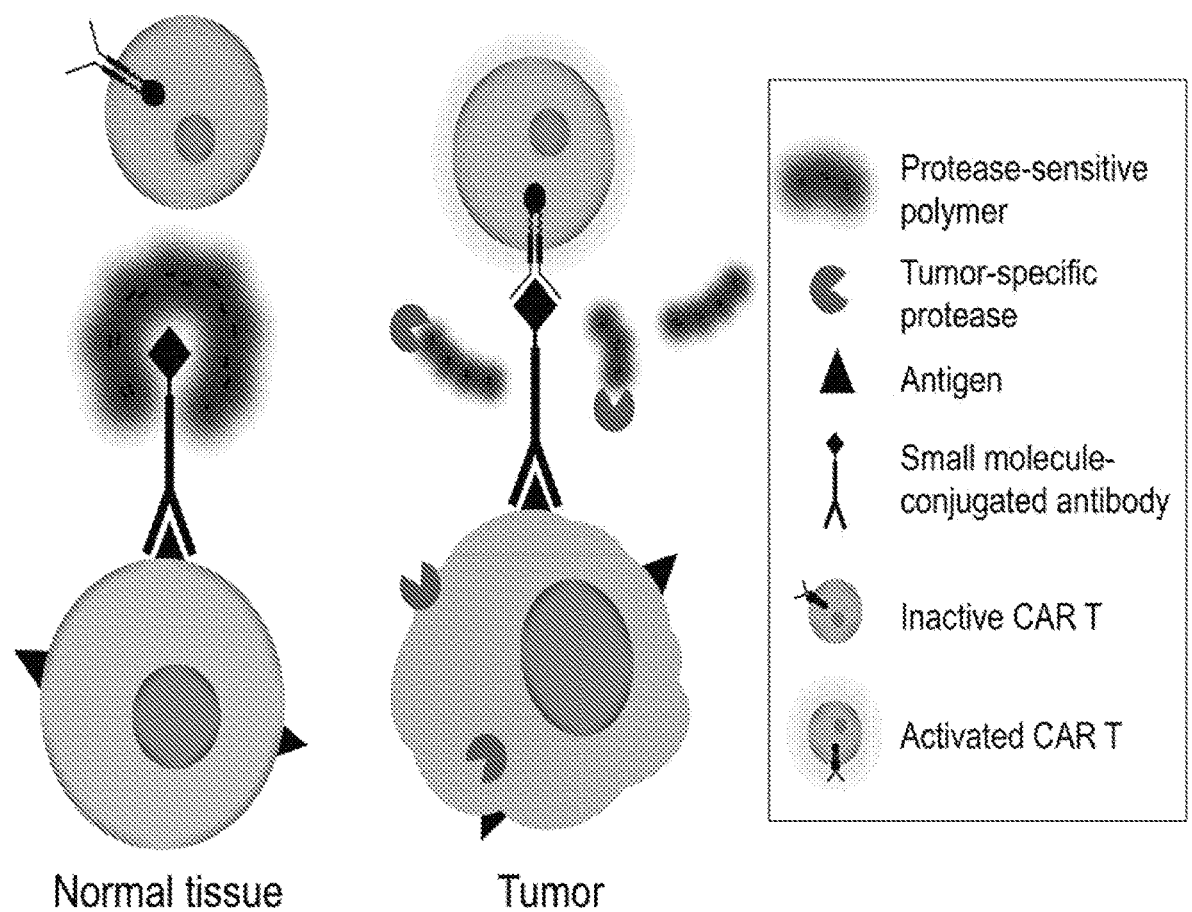
FIG. 1. Illustrates the protease-specific unmasking strategy to induce a tumor specific T-cell response.
Figure 2:
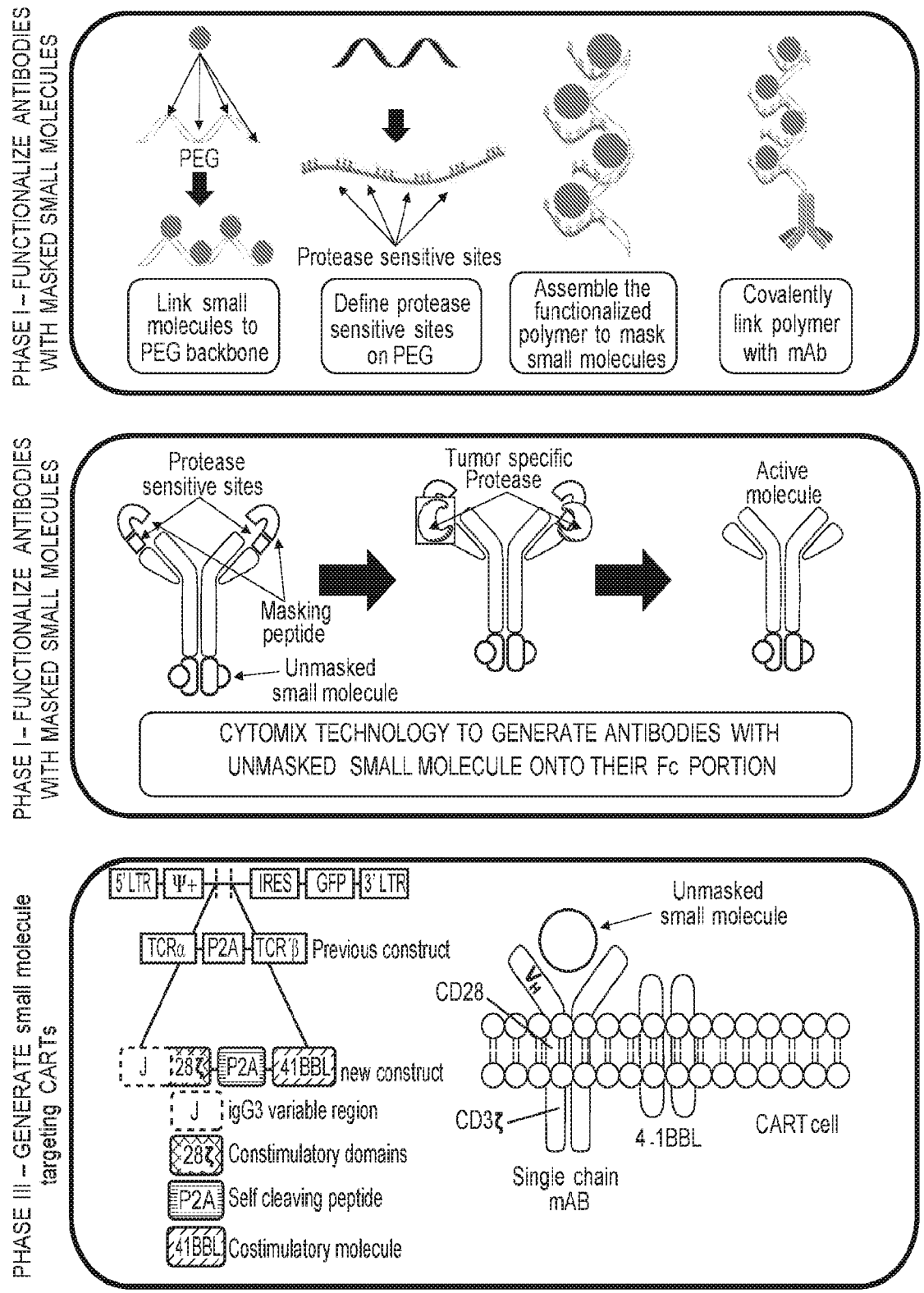
FIG. 2. Illustrates the universal CAR T cells directed against unmasked antigens for tumor-targeted immunotherapy.
Figure 3:
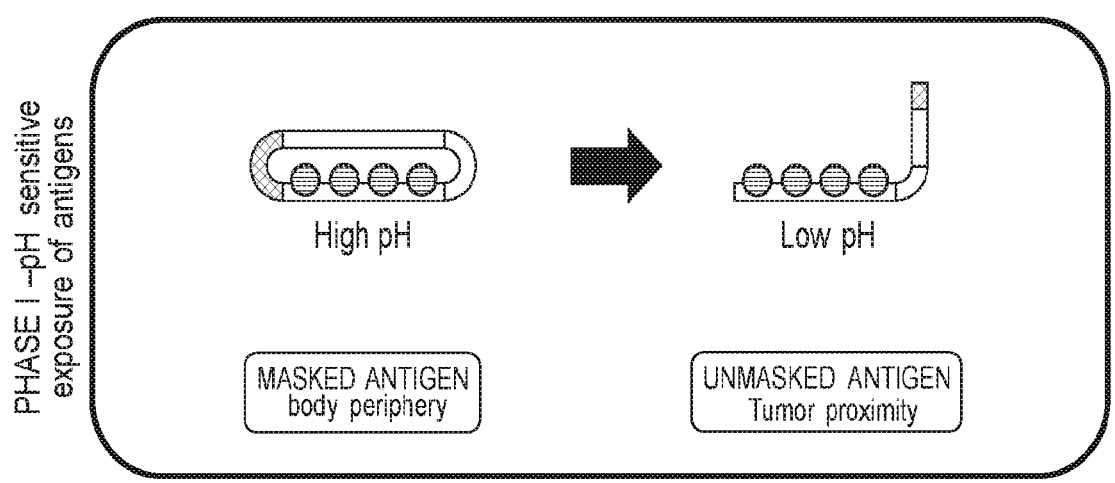
FIG. 3. Illustrates pH dependent unmasking of antigen.
Figure 6:
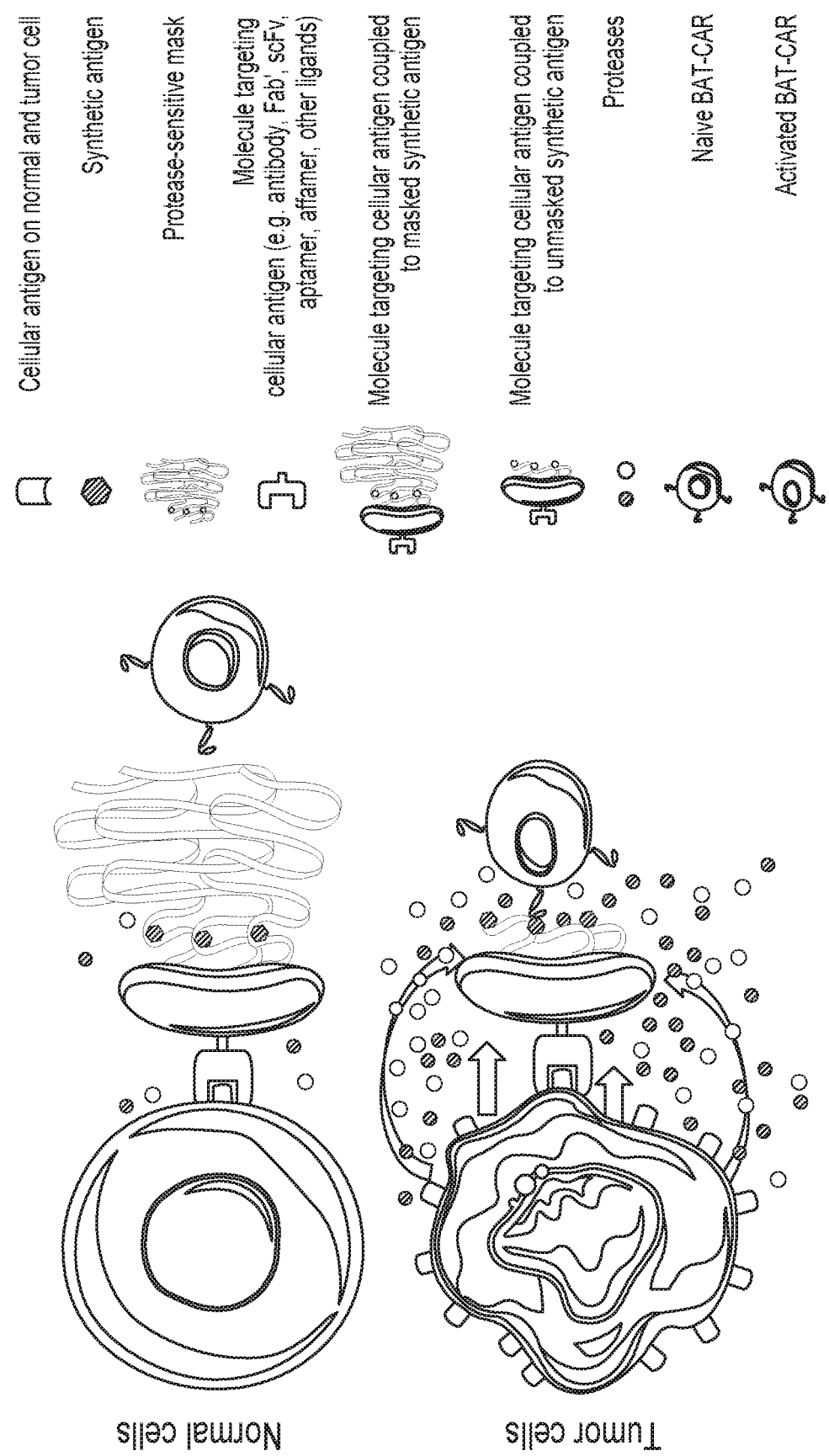
FIG. 6. Schematic presentation of the BAT-CAR strategy. A BAT-CAR is specific for a synthetic antigen, which is coupled to a tumor-targeting antibody. The synthetic antigen is protected from T cell recognition by a "mask" containing protease-sensitive sites. When the tumor-targeting antibody binds to tumors, tumor-derived proteases degrade the mask. Thus, the synthetic antigen becomes accessible for recognition by the BAT-CAR T cell, which, in turn, becomes activated to direct an immune response against the tumor.

The overarching strategy for is schematically presented in FIG. 1. A series of binary events determines whether CAR T cells will be activated by the synthetic small molecule. These Binary Activated T cells using Chimeric Antigen Receptors (BAT-CARs) should be completely inert in the absence of the small molecule and activated only at sites where the small molecule is unmasked. The systems and compositions of the invention can be tailored to direct T cell responses against any solid tumor in a patient-specific fashion.

Another aspect of this invention is that any chimeric cellular receptor can be engineered to be stimulated by administration of a small molecule. That is, fusion of a single-chain antibody with any cellular receptor, can produce novel chimeric receptors. Thus, administration of a small molecule recognized by the single chain antibody can stimulate downstream effects in the target cell characteristic of stimulating the receptor with its natural ligand. In the current invention, T cell receptor signaling can be enabled by administration of a small molecule. That is, administration of a small molecule recognized by the single-chain antibody fused to T cell signaling molecules (for example but not uniquely CD28 and CD3 zeta) leads to hallmark changes in T cells representative to T cell receptor signaling. By making chimeras of a small molecule binding single chain antibody with any cellular receptor, specific biological outcomes can be induced by administration of a small molecule recognized by the single chain antibody.

The reagents according to the invention generate a T cell-directed immune response specifically within a tumor without prior information on neoantigens. Tumors are targeted with a binding molecule for an antigen that is enriched but not necessarily unique to tumors. This binding molecule will be coupled to a pharmacologically inert small molecule. The small molecule serves as the target for a universal CAR T cell engineered with an extracellular binding domain that is specific for the small molecule. This universal CAR T cell referred to herein as a "Binary Activated T cells using Chimeric Antigen Receptors (BAT-CARs) is completely inert in the absence of the small molecule. Systemic treatment of the patient with the masked small molecule conjugated binding molecule will deliver the small molecule to the tumor, creating a unique target for the BAT-CARS. To prevent off target activation of the BAT-CAR T cell the small molecule is masked with a "triggering" polymer (e.g. enzyme sensitive or pH sensitive). While intact, the polymer prevents the small molecule from binding and activating the BAT-CAR T cell. However, the tumors locally secrete proteases that digest protease sensitive "triggering" polymer thus exposing the small molecule only at the site of the tumor. In the case of a pH sensitive tumor, the slightly acidic pH microenvironment of the tumor compared to physiologic pH, digest the pH-sensitive "triggering" polymer thus exposing the small molecule only at the site of the tumor An alternative approach, the binding site of the binding molecule will be masked with a triggering polymer such that binding to the tumor antigen will be inhibited. As in the case of the masked small molecule either tumor specific proteases or pH will digest the triggering polymer allowing the binding molecule to bind the tumor. The small molecule e binds and activates the BAT-CAR T cell Binding Molecule Binding molecules according to the invention have binding specify for a tumor antigen. A binding molecule is also referred to herein as a "tumor targeting unit". A binding molecule is able to bind to or otherwise associate with a biological entity, for example, a membrane component, a cell surface receptor, an antigen, or the like. The specificity of the binding molecule allows the binding molecule to become localized at a particular targeting site, for instance, a tumor, a disease site, a tissue, an organ, a type of cell, etc.

The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules that are able to bind to or recognize a binding partner (or a limited number of binding partners) to a substantially higher degree than to other, similar biological entities.

Binding molecules include but are not limited to antibody molecules, receptor ligands, peptides, haptens, aptamers, affimers, T-cell receptor tetramers and other targeting molecules known to those skilled in the art. For example, contemplated the binding molecule may include a nucleic acid, polypeptide, glycoprotein, carbohydrate, or lipid.

A binding molecule can be an antibody, which term is intended to include antibody fragments. For example, an antibody includes monoclonal antibodies, polyclonal antibodies, Fv, Fab, Fab' and F(ab')$_2$ immunoglobulin fragments, synthetic stabilized Fv fragments, e.g., single chain Fv fragments (scFv), disulfide stabilized Fv fragments (dsFv), single variable region domains (dAbs) minibodies, combibodies and multivalent antibodies such as diabodies and multi-scFv, single domains from camelids or engineered human equivalents. Antibodies are made either by conventional immunization (e.g., polyclonal sera and hybridomas), or as recombinant fragments, usually expressed in *E. coli*, after selection from phage display or ribosome display libraries. Alternatively, 'combibodies' comprising non-covalent associations of VH and VL domains, can be produced in a matrix format created from combinations of diabody-producing bacterial clones. The term "antibody" also includes any protein having a binding domain which is homologous or largely homologous to an immunoglobulin binding domain. Such proteins may be derived from natural sources, or partly or wholly synthetically produced.

For example, the binding molecule is an affimer. An affimer is a small, highly stable protein engineered to display peptide loops which provide a high affinity binding surface for a specific target protein. It is a protein of low molecular weight, 12-14 kDa, derived from the cysteine protease inhibitor family of cystatins. Affimer proteins are composed of a scaffold, which is a stable protein based on the cystatin protein fold. They display two peptide loops and an N-terminal sequence that can be randomized to bind different target proteins with high affinity and specificity similar to antibodies. Stabilization of the peptide upon the protein scaffold constrains the possible conformations which the peptide may take, thus increasing the binding affinity and specificity compared to libraries of free peptides.

For example, a binding molecule can be a nucleic acid binding molecule (e.g. an aptamer) that binds to a cell type specific marker. In general, an aptamer is an oligonucleotide (e.g., DNA, RNA, or an analog or derivative thereof) that binds to a particular target, such as a polypeptide. Aptamers are short synthetic single-stranded oligonucleotides that specifically bind to various molecular targets such as small molecules, proteins, nucleic acids, and even cells and tissues. These small nucleic acid molecules can form secondary and tertiary structures capable of specifically binding proteins or other cellular targets, and are essentially a chemical equivalent of antibodies. Aptamers are highly specific, relatively small in size, and non-immunogenic. Aptamers are generally selected from a biopanning method known as SELEX (Systematic Evolution of Ligands by Exponential enrichment) (Ellington et al. Nature. 1990; 346(6287):818-822; Tuerk et al., Science. 1990; 249(4968): 505-510: Ni et al., Curr Med Chem. 2011; 18(27):4206-14;

which are incorporated by reference herein in their entireties). Methods of generating an apatmer for any given target are well known in the art.

In some embodiments, a binding molecule may be a naturally occurring or synthetic ligand for a cell surface receptor.

In some embodiments, the targeting molecule is a carbohydrate. Carbohydrates may be natural or synthetic. A carbohydrate may be a derivatized natural carbohydrate. In some embodiments, the carbohydrate comprises monosaccharide or disaccharide, including but not limited to, glucose, fructose, galactose, ribose, lactose, sucrose, maltose, trehalose, cellbiose, mannose, xylose, arabinose, glucoronic acid, galactoronic acid, mannuronic acid, glucosamine, galatosamine, or neuramic acid. In some embodiments, the carbohydrate is a polysaccharide, such as, but not limited to, pullulan, cellulose, microcrystalline cellulose, hydroxypropyl methylcellulose (HPMC), hydroxvcellulose (HC), methylcellulose (MC), dextran, cyclodextran, glycogen, starch, hydroxyethylstarch, carageenan, glycon, amylose, chitosan, N,O-carboxymethylchitosan, algin and alginic acid, starch, chitin, heparin, konjac, glucommannan, pustulan, heparin, hyaluronic acid, curdlan, and xanthan. In some embodiments, the carbohydrate is a sugar alcohol, such as, but not limited to mannitol, sorbitol, xylitol, erythritol, maltitol, or lactitol.

By tumor antigen it is meant any cell surface molecule on a tumor cell. Preferably, the tumor antigen distinguishes tumor cells from normal cells. Tumor antigens can distinguish tumor cells from normal cell by being uniquely expressed on tumor cells or over-represented in tumor cells compared to normal cells. A tumor antigen is a polypeptide, a peptide (e.g. MHC peptide), a lipid, or a carbohydrate.

Exemplary tumor antigens include, but are not limited to Her2, prostate stem cell antigen (PSCA), alpha-fetoprotein (AFP), carcinoembryonic antigen (CEA), cancer antigen-125 (CA-125). CA19-9, calretinin. MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes: MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein.

Recognition Domain

The recognition domain serves as the target for a universal CAR T cell. The recognition domain is also referred to herein as an "antigen small molecule" The recognition domain is linked to the binding domain in such a manner as not to interfere with the ability of the binding domain to binds to its ligand. The recognition domain is non-human. The recognition domain is linked to the binding molecule directly. Alternatively, recognition domain is linked to the binding molecule indirectly (e.g., via the protection domain or a carrier domain). The recognition domain is one or more (i.e., plurality) of small molecules. The small molecule is synthetic or naturally-occurring. The small molecule is biologically active or inactive. As used herein, the phrase "biologically active" refers to a characteristic of any substance that has activity in a biological system and/or organism. For instance, a substance that, when administered to an organism, has a biological effect on that organism, is considered to be biologically active. Preferably the small molecule is non-immunogenic (i.e. preferentially non-antigenic).

In general, a "small molecule" is understood in the art to be an organic molecule that is less than about 5 kilodaltons (Kd) in size. In some embodiments, the small molecule is less than about 4 Kd, about 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol.

Exemplary small molecules that are useful in the production of recognition domains include fluorescein isothiocyanate (FITC), anthraquinone-2-acid, an amphetamine, a benzodiazepine, a benzoylecgonine, a buprenorphine, an opioid, a cannabinoid, a phencyclidine, a tricyclic antidepresst, dextromethorphan, fentanyl, meprobamate, methadone, methamphetamine, oxycodone, THC, tramadol, zolpidem, ketamine, LSD, MDMA, methaqualone, propoxyphene or norketimine. Other exemplary small molecules for use in the present invention include those listed at http://www.randox-toxicology.com/products.biochip-array and http://www.randoxtoxicology.com/products/biochip-array/doa-I.

Protection Domain

In various embodiments, the recognition domain is linked to a protection domain. The protection domain is also referred to herein as the "mask". The protection domain serves to mask the recognition domain to prevent the recognition domain from binding and activating the BAT CAR. The protection domain is in whole or in part enzyme (e.g., protease) sensitive or pH sensitive. In some embodiments the protection domain is composed of one or more enzyme (i.e., cleavable peptide) or pH susceptible sites. When an enzyme or pH susceptible site are exposed to enzymes, for instance, proteases, or a particular pH the reagent is cleaved, such that the recognition domain is unmasked.

The protection domain can be composed of any material or size as long as it can serve as a carrier or platform for the recognition domain and or the enzyme susceptible site. Preferably the material is non-immunogenic, i.e. does not provoke an immune response in the body of the subject to which it will be administered.

The protection domain is composed of in whole or in part of polymers or non-polymer materials.

The protection domain is linked directing to the binding molecule or indirectly via a carrier domain. Suitable carriers are knows in the art. In preferred embodiments, the carrier domain utilizes the Akrivis ADAPT™ Technology (See, WO/2014/100377. WO/2012/177775, and US 20140186850 the contents of which are herein incorporated by reference in their entireties).

In some aspects, the protection domain is composed of a masking peptide and a masking polymer. Optionally the protection domain further includes a detection domain.

A number of biodegradable and non-biodegradable biocompatible polymers are known in the field of polymeric biomaterials, controlled drug release and tissue engineering (see, for example, U.S. Pat. Nos. 6,123,727; 5,804,178; 5,770,417; 5,736,372; 5,716.404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera: U.S. Pat. No. 5,019,379 to Domb; U.S. Pat. No. 5,010,167 to Ron: U.S. Pat. No. 4,946,929 to d'Amore; and U.S. Pat. Nos. 4,806, 621; 4,638,045 to Kohn; see also Langer. Acc. Chem. Res. 33:94, 2000: Langer, J. Control Release 62:7, 1999: and Uhrich et al., Chem. Rev. 99:3181, 1999; all of which are incorporated herein by reference).

Polymers include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride and polystyrene.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In some embodiments the polymers are polyesters, polyanhydrides, polystyrenes, polylactic acid, polyglycolic acid, and copolymers of lactic and glycoloic acid and blends thereof.

PVP is a non-ionogenic, hydrophilic polymer having a mean molecular weight ranging from approximately 10,000 to 700,000 and the chemical formula $(C_6H_9NO)[n]$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™ Subtosan™, and Vinisil™. PVP is non-toxic, highly hygroscopic and readily dissolves in water or organic solvents.

Polyethylene glycol (PEG), also known as poly(oxyethylene)glycol, is a condensation polymer of ethylene oxide and water having the general chemical formula $HO(CH_2CH_2O)[n]H$.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water. PEG, PVA and PVP are commercially available from chemical suppliers such as the Sigma Chemical Company (St. Louis, Mo.).

In certain embodiments the particles may comprise poly(lactic-co-glycolic acid) (PLGA).

The enzyme susceptible site is dependent on enzymes that are active in a specific disease state. For instance, tumors are associated with a specific set of enzymes. If the disease state being analyzed is a tumor then the product is designed with an enzyme susceptible site that matches that of the enzyme expressed by the tumor or other diseased tissue. Alternatively, the enzyme specific site may be associated with enzymes that are ordinarily present but are absent in a particular disease state. In this example, a disease state would be associated with a lack or signal associated with the enzyme, or reduced levels of signal compared to a normal reference.

An enzyme, as used herein refers to any of numerous proteins produced in living cells that accelerate or catalyze the metabolic processes of an organism. Enzymes act on substrates. The substrate binds to the enzyme at a location called the active site just before the reaction catalyzed by the enzyme takes place. Enzymes include but are not limited to proteases, glycosidases, lipases, heparinases, phosphatases.

The enzyme susceptible site may be optimized to provide both high catalytic activity (or other enzymatic activity) for specified target enzymes but to also release optimized detectable markers for detection. Numerous other enzyme/substrate combinations associated with specific diseases or conditions are known to the skilled artisan and are useful according to the invention.

In some aspects the enzyme susceptible site is a peptide (also referred to herein as a "masking peptide". The masking peptide includes an enzyme cleavage site (i.e., cleavable peptide) and one or more sites capable of linking the masking polymer and the binding molecule (either directly or via a carrier domain).

In some aspects the masking peptide has the following formula: $(Aa_{N1})_{p1}(Aa_{N2})_{p2}(\text{CLEAVABLE PEPTIDE})_{q1}(Aa_{c1})_{q}Aa_{C2}$ In various aspects the amino acid sequence flanking the N-terminus of the cleavable peptide is of the general formula $(Aa_{N1})_{p1}(Aa_{N2})_{p2}$,
wherein:
p1 is an integer selected from 1 to 10;
p2 is an integer selected from 2 to 20;
$Aa_{N1}$, at each occurrence, is any amino acid, preferably independently selected from lysine, histidine, arginine, aspartic acid, and glutamic acid;
$Aa_{N2}$, at each occurrence, is any amino acid, preferably independently selected from serine, threonine, asparagine, glutamine, and glycine; and
$Aa_{N2}$ is linked to the N-terminus of the cleavable peptide through a peptide bond.

In one embodiment, p1 is 1, 2, 3, 4, 5, 6, 7, 8, 9, or 10. In one embodiment, p1 is 1, 2, 3, 4, or 5. In one embodiment, p1 is 6, 7, 8, 9, or 10. In one embodiment, p1 is 1, 2, or 3. In one embodiment, p1 is 1 or 2. In one embodiment, p1 is 1.

In one embodiment, $Aa_{N1}$, at each occurrence, is any amino acid, preferably independently selected from lysine, histidine, and arginine. In one embodiment, $Aa_{N1}$, at each occurrence, is independently selected from lysine and histidine. In one embodiment, $Aa_{N1}$, at each occurrence, is independently selected from lysine and arginine. In one embodiment, $Aa_{N1}$, at each occurrence, is independently selected from histidine and arginine. In one embodiment, $Aa_{N1}$, at each occurrence, is lysine. In one embodiment, Aa$_{N1}$, at each occurrence, is histidine. In one embodiment, Aa$_{N1}$, at each occurrence, is arginine.

In one embodiment, Aa$_{N1}$, at each occurrence, is independently selected from aspartic acid and glutamic acid. In one embodiment, Aa$_{N1}$, at each occurrence, is aspartic acid. In one embodiment, Aa$_{N1}$, at each occurrence, is glutamic acid.

In one embodiment, p1 is 1, and Aa$_{N1}$ is lysine. In one embodiment, p1 is 1, and Aa$_{N1}$ is histidine. In one embodiment, p1 is 1, and Aa$_{N1}$ is arginine. In one embodiment, p1 is 1, and Aa$_{N1}$ is aspartic acid. In one embodiment, p1 is 1, and Aa$_{N1}$ is glutamic acid.

In one embodiment, p1 is 2, and Aa$_{N1}$, at each occurrence, is independently selected from lysine, histidine, and arginine. In one embodiment, Aa$_{N1}$, at each occurrence, is independently selected from lysine and histidine. In one embodiment. Aa$_{N1}$, at each occurrence, is independently selected from lysine and arginine. In one embodiment, Aa$_{N1}$, at each occurrence, is independently selected from histidine and arginine.

In one embodiment, p1 is 2, and Aa$_{N1}$, at each occurrence, is independently selected from aspartic acid and glutamic acid.

In one embodiment, p2 is an integer selected from 2 to 10. In one embodiment, p2 is an integer selected from 11 to 20. In one embodiment, p2 is an integer selected from 2 to 5. In one embodiment, p2 is an integer selected from 5 to 10. In one embodiment, p2 is an integer selected from 11 to 15. In one embodiment, p2 is an integer selected from 15 to 20. In one embodiment, p2 is 2, 3, or 4. In one embodiment, p2 is 2 or 3. In one embodiment, p2 is 2.

In one embodiment. Aa$_{N2}$, at each occurrence, is any amino acid, preferably independently selected from serine, threonine, and glycine. In one embodiment, Aa$_{N2}$, at each occurrence, is independently selected from serine and glycine. In one embodiment, Aa$_{N2}$, at each occurrence, is independently selected from threonine and glycine. In one embodiment, Aa$_{N2}$, at each occurrence, is independently selected from serine and threonine. In one embodiment, Aa$_{N2}$, at each occurrence, is serine. In one embodiment, Aa$_{N2}$, at each occurrence, is threonine. In one embodiment, Aa$_{N2}$, at each occurrence, is glycine.

In one embodiment. Aa$_{N2}$, at each occurrence, is independently selected from asparagine, glutamine, and glycine. In one embodiment, Aa$_{N2}$, at each occurrence, is independently selected from asparagine and glycine. In one embodiment, Aa$_{N2}$, at each occurrence, is independently selected from glutamine and glycine. In one embodiment, Aa$_{N2}$, at each occurrence, is independently selected from asparagine and glutamine. In one embodiment, Aa$_{N2}$, at each occurrence, is asparagine. In one embodiment, Aa$_{N2}$, at each occurrence, is glutamine.

In various aspects, the amino acid sequence flanking the C-terminus of the cleavable peptide is of the general formula: (Aa$_{C1}$)$_q$Aa$_{C2}$,
wherein:
q is an integer selected from 2 to 20;
Aa$_{C1}$, at each occurrence, is any amino acid, preferably independently selected, from serine, threonine, asparagine, glutamine, and glycine;
Aa$_{C2}$ is any reactive group capable of linking the masking peptide to the masking polymer, binding domain or carrier domain.
Aa$_{C1}$ is linked to the C-terminus of the cleavable peptide through a peptide bond.

In one embodiment, q is an integer selected from 2 to 10. In one embodiment, q is an integer selected from 11 to 20.

In one embodiment, q is an integer selected from 2 to 5. In one embodiment, q is an integer selected from 5 to 10. In one embodiment, q is an integer selected from 11 to 15. In one embodiment, q is an integer selected from 15 to 20. In one embodiment, q is 2, 3, or 4. In one embodiment, q is 2 or 3. In one embodiment, q is 2.

In one embodiment, AaC1, at each occurrence, is any amino acid, preferably independently selected from serine, threonine, and glycine. In one embodiment, AaC1, at each occurrence, is independently selected from serine and glycine. In one embodiment, AaC1, at each occurrence, is independently selected from threonine and glycine. In one embodiment, AaC1, at each occurrence, is independently selected from serine and threonine. In one embodiment, Aa$_{C1}$, at each occurrence, is serine. In one embodiment, Aa$_{C1}$, at each occurrence, is threonine. In one embodiment, Aa$_{C1}$, at each occurrence, is glycine.

In one embodiment, Aa$_{C1}$, at each occurrence, is independently selected from asparagine, glutamine, and glycine. In one embodiment, Aa$_{C1}$, at each occurrence, is independently selected from asparagine and glycine. In one embodiment, Aa$_{C1}$, at each occurrence, is independently selected from glutamine and glycine. In one embodiment, Aa$_{C1}$, at each occurrence, is independently selected from asparagine and glutamine. In one embodiment, Aa$_{C1}$, at each occurrence, is asparagine. In one embodiment, Aa$_{C1}$, at each occurrence, is glutamine.

Aa$_{C2}$ is any reactive group capable of linking the masking peptide to the masking polymer, binding domain or carrier domain. For example, is a maleimide, an iodoacetamide, a thioester, an NHS ester, an imidoester, a hydroxymethyl phosphine, a carbodiimide, an anhydrides, a carbonate, an aldehydes, a glyoxal, a haloacetyl, a pyridyldisulfide, avinyl sulfone, an isocyanates, a carbonyldiimidazole, a bensophenone, an anthraquinone, a psoralen compound, an aryl azide, or a halogenated aryl. In a specific embodiment Aa$_{C2}$ is a cysteinamide. Conjugation chemistries are known in the art, see for example, Chemistry of Protein Conjugation and Cross-Linking, Shan S. Wong, CRC Press 1991, the content of which is incorporated by reference in its entirety)

q1 is an integer selected from 1 to 20. In one embodiment, q1 is 1, 2, 3, 4, 5, 6, 7, 8, 9, 10, 11, 12, 13, 14, 15, 16, 17, 18, 19, or 20. In one embodiment, q1 is 1, 2, 3, 4, 5, 6, 7, 8, 9, or 10. In one embodiment, q1 is 6, 7, 8, 9, or 10. In one embodiment, q1 is 1, 2, 3, 5 or 5. In one embodiment, p1 is 1 or 2. In one embodiment, q1 is 1.

The cleavable peptide contains an enzyme susceptible site capable of being cleaved by an enzyme secreted by a tumor. Enzymes secreted by tumors are known in the art and include e.g., proteases, lipases, glyosidases. Preferably, the enzyme susceptible site is a protease sensitive site. The protease is for example a cysteine protease, a serine protease, and aspartate protease or a threonine protease.

Cysteine proteases include for example, cathepsin B, L, H, or S, Calpain, MMP-1, MMP-2, MMP-7, MMP-9, or MMP-14. Serine proteases include for example, Trypsin, Hepsin, KLK6, KLK7, KLK8, Matriptase, SLP1, TMPRSS3, or PRSS3/mesotrypsin. Am aspartate protease includes for example, Cathepsin-D. A threonine protease includes for example, 26S proteasome.

In general, the cleavable peptides will be 150 residues or less, 100 residue or less or 50 residues or less. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 4-50 residues, 5-50 residues, 6-50 residues, 7-50 residues, 7-25, residues, 4-20 residues, 5-20 residues, 6-20 residues, 7-20 residues, and 7-15 residues are contemplated.

Exemplary cleavable peptides include peptides comprising the amino acid sequence PLGVRG (SEQ ID NO:11), PRCGVPDV (SEQ ID NO:12), PRCGNPDV (SEQ ID NO:13), PRCGXPD (where "X" is any amino acid, preferably "V") (SEQ ID NO:14), PRCGVPDL (SEQ ID NO:15), PRCGVPDK (SEQ ID NO:16) or GPICFFRLGK (SEQ ID NO:17).

In a preferred embodiment, the masking peptide comprises the amino acid sequence: LysSerGlyProLeuGlyValArgGlySerSerCys (SEQ ID NO:18). In another preferred embodiment, the masking peptide comprises the amino acid sequence: LysSerGlyProLeuGlyValArgGlySerSerCysteineamide (SEQ ID NO:19).

By "any amino acid" it meant the twenty conventional amino acids, tereoisomers (e.g., D-amino acids) of the twenty conventional amino acids and unnatural amino acid.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-, α-disubstituted amino acids. N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, for example, at least 90 percent sequence identity, at least 95 percent sequence identity, or at least 99 percent sequence identity.

In some embodiments, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Suitable conservative amino acids substitution groups are: valine-leucine-isoleucine, phenylalanine-tyrosine, lysine-arginine, alanine valine, glutamic-aspartic, and asparagine-glutamine.

A detection domain contains one or more detectable labels. As used herein, a "detectable label" is understood as a molecule that can be detected, preferably quantitatively, when present in a sample or subject, including, but not limited to, enzymatic label (e.g., alkaline phosphatase), fluorescent label, radioactive label, dense particle label, chemiluminescent label, bioluminescent label, prosthetic group label, fluorescence emitting metal atom, radioactive isotope, quantum dot, nanoparticle, electron-dense reagent, hapten, or biotin. Those of skill in the art will understand that the specific detectable label for use in a particular method will be determined, for example, on the target to be detected, the sample in which the detection is performed (e.g., liquid or solid sample, detection in vitro or in vivo), and the equipment available for detection. A detectable label can be detected directly, e.g., a fluorescent label. Alternatively, a detectable label can be detected by contacting the detectable label with at least one additional reagent, e.g., an enzyme substrate that produces a color, fluorescent, or luminescent product; a reagent that binds the non-sterically hindered tether, e.g., an avidin containing label for binding a biotin-containing tether, a nickel containing tether for binding 6.times.His; that is detected directly, e.g., a fluorescent or radioactive label, or indirectly, e.g., an enzyme.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

CARs

The CAR according to the invention generally comprises at least one transmembrane polypeptide comprising at least one extracellular ligand-binding domain and, one transmembrane polypeptide comprising at least one intracellular signaling domain; such that the polypeptides assemble together to form a Chimeric Antigen Receptor.

The term "extracellular ligand-binding domain" as used herein is defined as an polypeptide that is capable of binding a ligand. Preferably, the extracellular ligand-binding domain will be capable of binding the "unmasked" recognition domain. For example, the extracellular ligand-binding domain binds small molecule that makes up the recognition domain.

Extracellular ligand-binding domain include but are not limited to antibody molecules, receptor ligands, peptides, haptens, aptamers, affimers, T-cell receptor tetramers and other targeting molecules known to those skilled in the art. For example, contemplated the extracellular ligand-binding domain may include a nucleic acid, polypeptide, glycoprotein, carbohydrate, or lipid.

A extracellular ligand-binding domain can be an antibody, which term is intended to include antibody fragments. For example, an antibody includes monoclonal antibodies, polyclonal antibodies, Fv, Fab, Fab' and F(ab')$_2$ immunoglobulin fragments, synthetic stabilized Fv fragments, e.g., single chain Fv fragments (scFv), disulfide stabilized Fv fragments (dsFv), single variable region domains (dAbs) minibodies, combibodies and multivalent antibodies such as diabodies and multi-scFv, single domains from camelids or engineered human equivalents. Antibodies are made either by conventional immunization (e.g., polyclonal sera and hybridomas), or as recombinant fragments, usually expressed in *E. coli*, after selection from phage display or ribosome display libraries. Alternatively, 'combibodies' comprising non-covalent associations of VH and VL domains, can be produced in a matrix format created from combinations of diabody-producing bacterial clones. The term "antibody" also includes any protein having a binding domain which is homologous or largely homologous to an immunoglobulin binding domain. Such proteins may be derived from natural sources, or partly or wholly synthetically produced.

For example, the extracellular ligand-binding domain is an affimer. An affimer is a small, highly stable protein engineered to display peptide loops which provide a high affinity binding surface for a specific target protein. It is a protein of low molecular weight, 12-14 kDa, derived from the cysteine protease inhibitor family of cystatins. Affimer proteins are composed of a scaffold, which is a stable protein based on the cystatin protein fold. They display two peptide loops and an N-terminal sequence that can be randomized to bind different target proteins with high affinity and specificity similar to antibodies. Stabilization of the peptide upon the protein scaffold constrains the possible conformations which the peptide may take, thus increasing the binding affinity and specificity compared to libraries of free peptides.

For example, the extracellular ligand-binding domain can be a nucleic acid binding molecule (e.g., an aptamer) that binds to a cell type specific marker. In general, an aptamer is an oligonucleotide (e.g., DNA, RNA, or an analog or derivative thereof) that binds to a particular target, such as a polypeptide. Aptamers are short synthetic single-stranded oligonucleotides that specifically bind to various molecular targets such as small molecules, proteins, nucleic acids, and even cells and tissues. These small nucleic acid molecules can form secondary and tertiary structures capable of specifically binding proteins or other cellular targets, and are essentially a chemical equivalent of antibodies. Aptamers are highly specific, relatively small in size, and non-immunogenic. Aptamers are generally selected from a biopanning method known as SELEX (Systematic Evolution of Ligands by Exponential enrichment) (Ellington et al. Nature. 1990; 346(6287):818-822; Tuerk et al., Science. 1990; 249(4968): 505-510: Ni et al., Curr Med Chem. 2011; 18(27):4206-14; which are incorporated by reference herein in their entireties). Methods of generating an apatmer for any given target are well known in the art.

In some embodiments, a binding molecule may be a naturally occurring or synthetic ligand for a small molecule antigen.

In a preferred embodiment the transmembrane domain further comprises a stalk region between said extracellular ligand-binding domain and said transmembrane domain. The term "stalk region" used herein generally means any oligo- or polypeptide that functions to link the transmembrane domain to the extracellular ligand-binding domain. In particular, stalk regions are used to provide more flexibility and accessibility for the extracellular ligand-binding domain. A stalk region may comprise up to 300 amino acids, preferably 10 to 100 amino acids more preferably 25 to 50 amino acids and most preferably 3 to 15 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain The signal transducing domain or intracellular signaling domain of the CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCR zeta, FcR gamma. FcR beta. FcR epsilon. CD3 gamma. CD3 delta. CD3 epsilon, CD5, CD22, CD79a. CD79b and CD66d. In a preferred embodiment, the signaling transducing domain of the CAR can comprise the CD3 zeta signaling domain, or the intracytoplasmic domain of the Fc epsilon RI beta or gamma chains. In another preferred embodiment, the signaling is provided by CD3 zeta together with co-stimulation provided by CD28 and a tumor necrosis factor receptor (TNFr), such as 4-1BB or OX40), for example.

In particular embodiment the intracellular signaling domain of the CAR of the present invention comprises a co-stimulatory signal molecule. In some embodiments the intracellular signaling domain contains 2, 3, 4 or more co-stimulatory molecules in tandem. A co-stimulatory molecule is a cell surface molecule other than an antigen receptor or their ligands that is required for an efficient immune response.

"Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD-3ζ CD27, CD28, 4-1BB, OX40, CD30, CD40, PD-1, ICOS, lymphocyte function-associated antigen-1 (LFA-1), CD2, CD7. LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class 1 molecule. BTLA and Toll ligand receptor. Examples of costimulatory molecules include CD-3ζ CD27, CD28, CD8, 4-1BB (CD137), -1BBL OX40, CD30, CD40, PD-1, ICOS, lymphocyte function-associated antigen-1 (LFA-1), CD2, CD7, LIGHT. NKG2C, B7-H3 and a ligand that specifically binds with CD83 and the like. In another particular embodiment, said signal transducing domain is a TNFR-associated Factor 2 (TRAF2) binding motifs, intra-cytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

The distinguishing features of appropriate transmembrane polypeptides comprise the ability to be expressed at the surface of an immune cell, in particular lymphocyte cells or Natural killer (NK) cells, and to interact together for directing cellular response of immune cell against a predefined target cell. The different transmembrane polypeptides of the CAR of the present invention comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein.

The term "a part of" used herein refers to any subset of the molecule, that is a shorter peptide. Alternatively, amino acid sequence functional variants of the polypeptide can be prepared by mutations in the DNA which encodes the polypeptide. Such variants or functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity. The functionality of the CAR of the invention within a host cell is detectable in an assay suitable for demonstrating the signaling potential of said CAR upon binding of a particular target. Such assays are available to the skilled person in the art. For example, this assay allows the detection of a signaling pathway, triggered upon binding of the target, such as an assay involving measurement of the increase of calcium ion release, intracellular tyrosine phosphorylation, inositol phosphate turnover, or interleukin (IL) 2, interferon gamma., GM-CSF, IL-3, IL-4 production thus effected.

Cells

Embodiments of the invention include cells that express a CAR (i.e., CARTS). The cell may be of any kind, including an immune cell capable of expressing the CAR for cancer therapy or a cell, such as a bacterial cell, that harbors an expression vector that encodes the CAR. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed." which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell, including a helper T cell (Th), a cytotoxic T cell (also known as TC, Cytotoxic T Lymphocyte, CTL, T-Killer cell, cytolytic T cell, CD8+ T-cells or killer T cell) a regulatory T cell (Treg), a T follicular regulatory cell (TFR), NK cells and NKT cells are also encompassed in the invention.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells can be autologous cells, syngeneic cells, allogenic cells and even in some cases, xenogeneic cells.

In many situations one may wish to be able to kill the modified CTLs, where one wishes to terminate the treatment, the cells become neoplastic, in research where the absence of the cells after their presence is of interest, or other event. For this purpose one can provide for the expression of certain gene products in which one can kill the modified cells under controlled conditions, such as inducible suicide genes.

Armed CARTS

The invention further includes CARTS that are modified to secrete one or more polypeptides. The polypeptide can be for example an antibody or cytokine. Cytokines included for example IL-2.

Armed CARTS have the advantage of simultaneously secreting a polypeptide at the targeted site, e.g. tumor site, graft site or autoimmune site.

Armed CART can be constructed by including a nucleic acid encoding the polypeptide of interest after the intracellular signaling domain. Preferably, there is an internal ribosome entry site, (IRES), positioned between the intracellular signaling domain and the polypeptide of interest. One skilled in the art can appreciate that more than one polypeptide can be expressed by employing multiple IRES sequences in tandem.

Introduction of Constructs into Cells

Expression vectors that encode the CARs can be introduced as one or more DNA molecules or constructs, where there may be at least one marker that will allow for selection of host cells that contain the construct(s).

The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the cell (i.e., T-cell) by any convenient means. The constructs may be integrated and packaged into non-replicating, defective viral genomes like Adenovirus, Adeno-associated virus (AAV), or Herpes simplex virus (HSV) or others, including retroviral vectors or lentiviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example) can knock-out an endogenous gene and replace it (at the same locus or elsewhere) with the gene encoded for by the construct using materials and methods as are known in the art for homologous recombination. For homologous recombination, one may use either OMEGA, or O-vectors. See, for example, Thomas and Capecchi. Cell (1987) 51, 503-512: Mansour, et al., Nature (1988) 336, 348-352; and Joyner, et al., Nature (1989) 338, 153-156.

The constructs may be introduced as a single DNA molecule encoding at least the CAR and optionally another gene, or different DNA molecules having one or more genes. Other genes include genes that encode therapeutic molecules or suicide genes, for example. The constructs may be introduced simultaneously or consecutively, each with the same or different markers.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

Methods of Use

The reagents according to the invention can be used for treating cancer, or other immunological disorders such as graft vs host disease or autoimmune disorders in a patient in need thereof. In another embodiment, reagents according to the invention can be used in the manufacture of a medicament for treatment of a cancer, or other immunological disorders such as graft vs host disease or autoimmune disorders in a patient in need thereof.

The present invention relies on methods for treating patients in need thereof, said method comprising at least one of the following steps: (a) providing a binding molecule having specificity for a tumor antigen wherein the binding molecule comprises a non-recognition domain linked to protection domain (b) providing a chimeric antigen receptor cell (CART) comprising an intracellular signaling domain, a transmembrane domain and an extracellular domain capable of specifically binding the recognition domain and administrating to the patient.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of T-cells, typically obtained from donors, into non-alloreactive cells. This may be done under standard protocols and reproduced as many times as needed. The resulted modified T cells may be pooled and administrated to one or several patients, being made available as an "off the shelf" therapeutic product.

Cells that can be used with the disclosed methods are described in the previous section. Said treatment can be used to treat patients diagnosed with cancer, autoimmune disorders or Graft versus Host Disease (GvHD). Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD): therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Administration of Cells

The invention is particularly suited for allogenic immunotherapy, insofar as it enables the transformation of T-cells, typically obtained from donors, into non-alloreactive cells. This may be done under standard protocols and reproduced as many times as needed. The resulted modified T cells may be pooled and administrated to one or several patients, being made available as an "off the shelf" therapeutic product.

Depending upon the nature of the cells, the cells may be introduced into a host organism, e.g., a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

In some embodiments, the cells are encapsulated to inhibit immune recognition and placed at the site of the tumor.

The cells may be administered as desired. Depending upon the response desired, the manner of administration, the life of the cells, the number of cells present, various protocols may be employed. The number of administrations will depend upon the factors described above at least in part.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient would be monitored for the proper dosage for the individual, and such practices of monitoring a patient are routine in the art.

Nucleic Acid-Based Expression Systems

The CARs of the present invention may be expressed from an expression vector. Recombinant techniques to generate such expression vectors are well known in the art.

Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example. Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5 prime' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals In certain embodiments of the invention, the use of internal ribosome entry sites (IRES) elements are used to create multigene, or polycistronic, messages, and these may be used in the invention.

In certain embodiments of the invention, the use 2A self cleaving peptides are used to create multigene, or polycistronic, messages, and these may be used in the invention.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species, pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may be a viral vector that encodes one or more CARs of the invention. Non-limiting examples of virus vectors that may be used to deliver a nucleic acid of the present invention are described below.

Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

AAV Vectors

The nucleic acid may be introduced into the cell using adenovirus assisted transfection. Increased transfection efficiencies have been reported in cell systems using adenovirus coupled systems (Kelleher and Vos, 1994: Cotten et al., 1992; Curiel, 1994). Adeno associated virus (AAV) is an attractive vector system for use in the cells of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986: Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviral Vectors

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding the desired sequence) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996: Zufferev et al., 1997; Blomer et al., 1997: U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other Viral Vectors

Other viral vectors may be employed as vaccine constructs in the present invention. Vectors derived from viruses such as vaccinia virus (Ridgeway, 1988: Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988: Baichwal and Sugden, 1986: Coupar et al., 1988; Horwich et al., 1990).

Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via asialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Vector Delivery and Cell Transformation

Suitable methods for nucleic acid delivery for transfection or transformation of cells are known to one of ordinary skill in the art. Such methods include, but are not limited to, direct delivery of DNA, RNA or mRNA such as by ex vivo transfection, by injection, and so forth. Through the application of techniques known in the art, cells may be stably or transiently transformed.

Ex Vivo Transformation

Methods for transfecting eukaryotic cells and tissues removed from an organism in an ex vivo setting are known to those of skill in the art. Thus, it is contemplated that cells or tissues may be removed and transfected ex vivo using nucleic acids of the present invention. In particular aspects, the transplanted cells or tissues may be placed into an organism. In preferred facets, a nucleic acid is expressed in the transplanted cells.

Kits of the Invention

Any of the compositions described herein may be comprised in a kit. In a non-limiting example, one or more cells for use in cell therapy and/or the reagents to generate one or more cells for use in cell therapy that harbors recombinant expression vectors may be comprised in a kit. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile, pharmaceutically acceptable buffer and/or other diluent.

In particular embodiments of the invention, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes a CAR as described herein and/or regulatory elements therefor.

In particular embodiments, there are one or more apparatuses in the kit suitable for extracting one or more samples from an individual. The apparatus may be a syringe, scalpel, and so forth.

In some cases of the invention, the kit, in addition to cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

Combination Therapy

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with other therapies. In the context of the present invention, it is contemplated that cell therapy could be used similarly in conjunction with chemotherapeutic, radiotherapeutic, or immunotherapeutic intervention, as well as pro-apoptotic or cell cycle regulating agents.

Alternatively, the present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

It is expected that the treatment cycles would be repeated as necessary. It also is contemplated that various standard therapies, as well as surgical intervention, may be applied in combination with the inventive cell therapy.

Chemotherapy

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, famesyl-protein tansferase inhibitors, transplatinum, 5-fluorouracil, vincristin, vinblastin and methotrexate, or any analog or derivative variant of the foregoing and also combinations thereof.

In specific embodiments, chemotherapy for the individual is employed in conjunction with the invention, for example before, during and/or after administration of the invention Radiotherapy Other factors that cause DNA damage and have been used extensively include what are commonly known as gamma-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy other than the inventive therapy described herein could thus be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include PD-1, PD-L1, CTLA4, carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor: interferon alpha, beta, and gamma; IL-2 and other cytokines: F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Definitions

As used herein, the term "biocompatible" refers to substances that are not toxic to cells. In some embodiments, a substance is considered to be "biocompatible" if its addition to cells in vivo does not induce inflammation and/or other adverse effects in vivo. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death.

As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes. For example an exemplary biodegradable material requires the presence of an enzyme for its degradation. Physiological conditions are not enough for the degradation of many (if not all) the biodegradable materials.

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. In some embodiments, the moieties are attached to one another by one or more covalent bonds. In some embodiments, the moieties are attached to one another by a mechanism that involves specific (but non-covalent) binding (e.g. streptavidin/avidin interactions, antibody/antigen interactions, etc.). In some embodiments, a sufficient number of weaker interactions can provide sufficient stability for moieties to remain physically associated.

As used herein, the terms "conjugated," "linked." and "attached," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used. e.g., physiological conditions. Typically the moieties are attached either by one or more covalent bonds or by a mechanism that involves specific binding. Alternately, a sufficient number of weaker interactions can provide sufficient stability for moieties to remain physically associated.

The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules that are able to bind to or recognize a binding partner (or a limited number of binding partners) to a substantially higher degree than to other, similar biological entities.

EXAMPLES

Example 1: Functionalize Tumor Targeted Antibodies with Masked Small Molecules The goal of this example is to construct a scaffold consisting of a backbone structure polymer structure coupled to small molecules, which can be further modified with a protease sensitive hydrogel polymer. PEG is a good choice for functionalizing the small molecules scaffold because it stabilizes biomolecules, it is resistant to degradation and the coupling chemistries are established. Any number of small molecules can be chosen. This scaffold of PEG/small molecule/protease sensitive hydrogel polymer will be coupled to a tumor targeted antibody.

Example 2: Functionalize Tumor Targeted Antibodies with Masked Small Molecules The goal this example is to use a Probody® CytomX technology which uses protease sensitive peptides to block the tumor targeting antibody's ability to recognize its antigen. In this strategy the small molecule is expected to be directly coupled to the Fc portion of the antibody or to some other site outside of the antigen recognition portion of the antibody. We will select the small molecule based on its pharmacological activity.

Example 3: Creation of a pH-Dependent Polymer to Unmask Small Molecules Only in Proximity of a Tumor The general strategy for this technology is development of a peptide whose conformation is altered in a pH dependent fashion. We plan to covalently link small molecules antigens to this peptide. Under physiologic conditions, the peptide will fold back on itself to mask the small molecule. Under acidic conditions, the peptide will open, unmasking the small molecules. The advantage of the strategy is that antibodies not bound to the tumor will mask the small molecules blocking inappropriate and unintended activation of the immune system. The general strategy for linking the hydrogel polymer to the tumor targeting antibody in Phase I will be adapted to linking this peptide to the tumor-targeting antibody. As alternative strategy, this pH-sensitive peptide can be directly injected into a tumor to generate an immune response.

Example 4: Engineer Car T Cells Directed Against Small Molecules

Material and Methods

The goal of this experiment was to engineer a CAR T cell that can be triggered by a small molecule either directly coupled to a tumor-targeting antibody or embedded in the protease sensitive polymer coupled to the tumor-targeting antibody. The CAR T cell was engineered with a single-chain antibody recognizing the small molecule. The chimera was constructed using CD8α leader sequence, CD8α hinge sequence, CD28, 4-1BB and CD3ζ intracellular domain fusions. FIG. 7 visualizes the composition of the CAR modules used herein.

Generation of CAR Constructs

The molecule design was inspired by the publication by Sun et al., Breast Cancer Res. 16(3):R61 (2014); where an anti-HER2 antibody was fused between the CD8α leader sequence and the CD8α hinge sequence and followed by the intracellular domains of CD28 and CD3ζ. Compared to the publication, the 4-1BB intracellular domain was inserted between CD28 and CD3ζ. Furthermore, without the use of any linker or spacer.

Two single-chain antibodies were cloned into such construct: an anti-FITC antibody, as described by Boder et al., Proc Natl Acad Sci USA. 26; 97(20): 10701-5, (2000), and an anti-anthraquinone-2-carboxylic acid, as designed by Randox Biosciences (Admore, Diamond Road, United Kingdom).

This CAR T is expected to interact with any small-molecule, provided the proper single-chain antibody.

Each construct was cloned by Gibson assembly and sequenced with traditional sequences services (GENEWIZ, Inc.).

Generation of Ecotropic Retrovirus

The retroviral vector we have chosen for proof of concept is based on the vector described by Hoist et al. J. Gen. Virol. 88: 1708-1716 (2007) and available through Addgene (plasmid #52107). Briefly, the CAR construct is inserted in an empty retroviral vector containing the MSCV's ψ sequence and a C-terminal GFP reporter gene, which is separated from the CAR sequence by a self-cleaving IRES module.

The ecotropic retrovirus was generated with the use of the PLAT-E packaging cell line (Cell Biolabs, Inc.), as described by the producer. Briefly, Plat-E cells were expanded in DMEM, 10% fetal calf serum (FCS), 1 µg/mL puromycin, 10 µg/mL blasticidin, penicillin and streptomycin. One day before transfection, the cells were let grow on 150 mm tissue culture plates (Falcon, #353025) until 70% confluency, in DMEM, 10% (FCS). On the day of transfection, 2.0 ml of Opti-MEM (ThermoFisher Scientific, #31985070) were mixed with 112.5 µl of Lipofectamine 2000 (Invitrogen, #11668500) and incubated for 10 minutes at room temperature. Afterwards, 30 µg of plasmid were added and the mixture, which was left incubate at room temperature for 15 further minutes. The Opti-MEM/lipofectamine 2000/DNA solution was added dropwise throughout the cell culture with a spiral movement. The cells were kept in incubation at 37° C./5% $CO_2$ for 48 hours. At harvest, the supernatant was collected and filtered through a 0.45 µm polyethersulfone (PES) filter (CELLTREAT Scientific Products, #229749). The filtered solution was split in two aliquots: one aliquot was used for immediate transduction of mouse T cells and one aliquot was aliquoted and stored at −80° C.

Transduction of Mouse Hybridoma T Cells

Mouse hybridoma T cells (58C) deprived of TCR α and β chains were used to study T cell activation upon antigen unmasking (Letourneur and Malissen, Eur J Immunol. December; 19(12):2269-74, (1989)).

The murine T cells were expanded in RPMI 10% FBS with penicillin and streptomycin. On the day of transduction 300.000 cells were seeded in the wells of a 6-well Costar plate (Corning, #3516). To each well, it was added 1 ml of virus supernatant, containing 5 µg ml$^{-1}$ polybrene (Santa Cruz Biotechnology, #sc-134220). After gentle mixing of the cells with the virus supernatant, the cells were centrifuged for one hour at 37° C. and 800 g in a Sorvall RT1 centrifuge (ThermoFisher, #EW-17705-10). After centrifugation, the viral supernatant was replaced with 2 ml of RPMI 10% FBS with penicillin and streptomycin. The remaining aliquot of virus supernatant was stored overnight at 4° C. After 16-24 hours, a new spin-infection was performed with 1 ml of the same virus supernatant previously stored at 4° C. The transduced cells were harvested and sorted for GFP positive cells after 48 hours incubation at 37° C./5% $CO_2$.

Quantification of T Cell Activation as a Function of CD69 Surface Expression

The wells of a 24-well Falcon plate (Corning, #353047) were coated with 500 µl of a 10 µg ml$^{-1}$ antigen solution in PBS for 1 hour at 37° C. The antigen solution contained a peptide bound to the antigen small molecule: BSA-FITC (Life Technologies, #A23015) for the anti-FITC CAR T cell and the post-cleavage peptide bond to anthraquinone-2-ate (pCP(AQ), SEQ ID NO: 1) for the anti-anthraquinone CAR T (anti-AQ CAR T). As mock, BSA (Sigma-Aldrich, #A7906) was used to coat the wells in every experiment involving CAR T cells. After the coating. 500,000 58 C in 500 µl cells RPMI 10% FBS with penicillin and streptomycin were seeded in each well. 58C cells and were incubated in the presence of their antigen for 4 hours at 37° C. before FACS analysis Prior to FACS analysis, 250 µl of cell solution were transferred to a 96-well Falcon plate with round bottom (Corning, #353077). Each plate was centrifuged 3 minutes at 500 g and 4° C. (ThermoFisher, #EW-17705-10). After removal of the supernatant, 250 µl of PBS 2% FBS were added to each well. The cells were mixed and the plate newly centrifuged for 3 minutes at 500 g and 4° C. (ThermoFisher, #EW-17705-10). After removal of the supernatant, 100 µl of PBS 2% FBS antibody solution were added to each well. Antibody staining was performed for 30 minutes on ice. To wash the cells from unbound antibody, 150 µl PBS 2% FBS were added to each well. The plates were centrifuged for 3 minutes at 500 g and 4° C. (ThermoFisher, #EW-17705-10) and the supernatant removed. Finally, 200 µl PBS 2% FBS were added to each well and prior FACS analysis the solutions were filtered into Falcon FACS tubes (Corning, #352235).

CD69 was detected with a Pacific Blue anti-mouse CD69 (Biolegend #104524). As isotype control we utilized Pacific Blue Armenian Hamster IgG isotype Ctrl (Biolegeng #400925).

Results

CD69 surface expression generated by the different CAR construct was tested. The data are presented in FIG. 8. Relative counts for this and subsequent figures, were calculated relative to the mode.

FIG. 8. FACS analysis of a population of 58C cells transduced with the appropriate anti-small molecule BAT-CAR T cell.CD69 was quantified as a result of CAR T cell activation upon antigen engagement. CD69 expression was triggered only when the mouse hybridoma T cell was engineered with either anti-FITC CAR T (SEQ ID NO: 10) on a or anti-anthraquino-2-ate (anti-AQ, SEQ ID NO: Y) to recognize the small molecule. No activation was observed when samples of naïve 58C cells or 58C cells transduced with an empty pMIG vector were exposed to the antigens. Neither anti-FITC CAR T cells or anti-AQ CAR T cells were activated in the presence of BSA. Effector=mouse hybridoma T cell engineered with CARs. Target=Antibody cognate antigen coating the well of a 24-well plate.

Example 5: Generation of MMP2 Sensitive Polymer for Antigen Unmasking

Materials and Methods

The goal of the experiment was to verify that a chemically synthesized peptide could be cleaved by its cognate matrix metalloprotease (MMP), for example MMP2 or MMP9. The peptide can be cleaved as free in solution or coupled, either directly or indirectly, to the tumor targeting unit. The peptide was designed to be coupled to the antigen small molecule and is meant to be a bridging block between the targeting unit and the masking PEG polymer.

Definition of a Masking Peptide Coupled to the Anthraquinone Small Molecule

The chosen peptide "CP(AQ)" (SEQ ID NO: 2) contains at its center the MMP2 cleavage sequence "ProLeuGlyValArgGly" (SEQ ID NO: 20) as described by Bremer et al., Nat Med. Jun, 7(6):743-8. (2001), with the cleavage site located between Gly and Val.

CP(AQ) synthesized sequence was "Lys(AQ)SerGlyProLeuGlyValArgGlySerSerCys" (SEQ ID NO: 2): the first residue "Lys" is covalently bound to the antigen small molecule anthraquinone-2-acid through its γ amino group. "SerGly" and "SerSer" surround its N-terminus and C-terminus, respectively, in order to provide the peptide with accessibility to the protease, flexibility and increase solubility in aqueous solutions. Finally, anthraquinone-2-acid was coupled to the lysine, on the peptide N-terminus. To provide a specific orientation during coupling of the peptide with the remaining platform components (e.g. tumor targeting unit and PEG masking polymer), the cleavable peptide's traditional free amino group at its N-terminus was maintained but at its C-terminus it was added L-cysteinamide. The amine is used for coupling onto NHS activated esters and L-cysteinamide for direct coupling against maleimides.

Validation of Peptide Cleavage by MMP2

Figure 9:
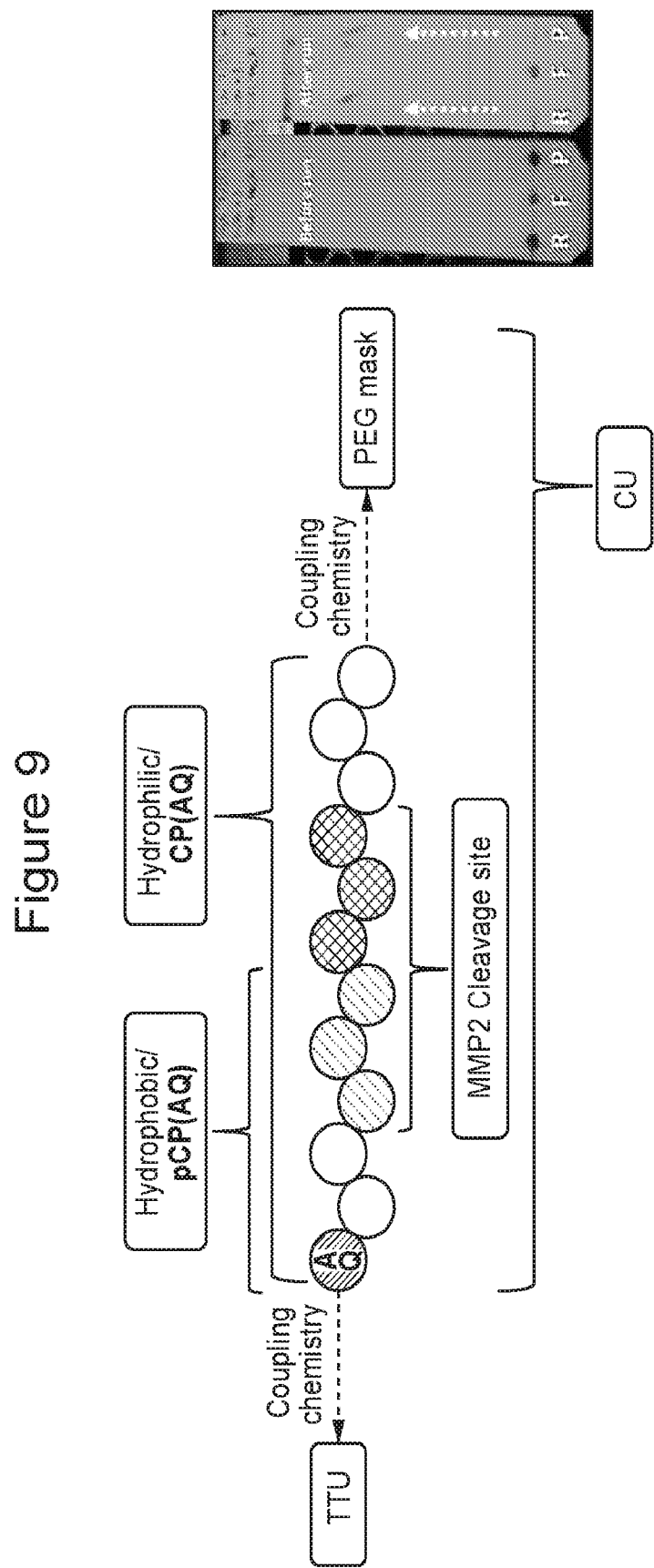
FIG. 9. Schematic presentation of the cleavable peptide structure, coupling strategy to the BAT-CAR platform and chemical properties of the cleavable peptide carrying an anthraquinone-2-ate molecule (CP(AQ)) or of the post-cleavage peptide carrying the same molecule (pCP(AQ)).

Thin layer chromatography (TLC) on UV fluorescent foils (Sigma-Aldrich, #70643) was performed to separate and to follow peptide proteolysis by spiked-in commercial MMP2 (BioLegend, #554304) over time (FIG. 9).

In order to follow the proteolysis of CP(AQ) by MMP2, we obtained an aliquot of the post-cleavage peptide "Lys (AQ)SerGly ProLeuGly" (pCP(AQ), SEQ ID NO: 1) to use as reference during the TLC run.

A mobile phase composed of a mixture of $CH_2Cl_2$: MeOH=3:1 (Sigma-Aldrich) was found suitable for the separation of pCP(AQ) from CP(AQ). TLC was found appropriate for this experiment because both pCP(AQ) and CP(AQ) are covalently bound to anthraquinone-2-acid which absorbs light in the UV range thus, quenching the fluorescence of the plate. Furthermore, CP(AQ) carries a positively charged arginine which increases significantly the fragment polarity, when compared to the post-cleavage peptide pCP(AQ).

The proteolysis reaction was carried on at 37° C., under moderate shaking, in 50 mM Borate Buffer, pH 7.5, 5 mM $CaCl_2$ (Seltzer et al. J Biol Chem. November 25:265(33): 20409-13, (1990). To this buffer, 100 μg of C(AQ) with 0.2 μg of purified, recombinant MMP2 in 100 μl reaction buffer were added. At regular time points, 1.5 μl of reaction aliquots were loaded directly at the starting line. Together with the reaction sample, two more solutions were prepared: one with 100 μg CP(AQ) in 100 μl reaction buffer and one with 100 μg pCP(AQ) in 100 μl reaction buffer. Both solutions were used as reference during the resolution of the reaction sample and as degradation control. The reaction was followed under the UV light of a traditional laboratory clean bench. Pictures of the plate, before and after the run, were taken with a personal mobile phone (Apple, iPhone 5S).

Results

The result of CP(AQ) proteolytic cleavage by MMP2 is shown in FIG. 9. The comparison of the spot intensity before and after the TLC run show that, after the incubation of CP(AQ) with MMP2, the compound was able to shift organic solution, with a transformed behavior from hydrophilic to hydrophobic (FIG. 9B, spot R), pCP(AQ) and CP(AQ) assume identical and opposite behavior, respectively (FIG. 9B, spots F and P).

Example 6: Targeting of a Tumor Antigen by the BAT-CAR Platform

Materials and Methods

The goal of the experiment was to verify that the BAT-CAR platform was able to target its tumor antigen through its targeting unit, either alone or in association to its antigen carrier domain. The BAT-CAR platform is modular and it can be divided in two main domains: a tumor targeting unit (TTU) and an antigen carrier unit (CU). The platform structure components are presented in FIG. 10.

The TTU, in turn, is divided in two domains: the tumor targeting peptide and the TTU-CU linking region. The tumor targeting peptide can be composed of an antibody against a tumor antigen but it can also be composed of any peptide that can recognize with sufficient specificity a protein overexpressed on carcinoid cells. If an antibody, the targeting unit can be a full-length IgG antibody, a single chain antibody (scFv) or the proteolytic product of a natural IgG that results in a fragment antigen-binding region (Fab). In the present example, the tumor targeting peptide is the antibody trastuzumab (Genentech Inc., Herceptin). The TTU-CU linking region is composed of a divalent antibody that can recognize the constant region in trastuzumab from one side and a specific epitope on CU on the other. In the present experiment, the TTU was incubated with Alexa fluor 647 (ThermoFisher Scientific. #A20347) to permit TTU tracking via flow cytometry (AMH).

The CU can be split in four regions: a peptide backbone, a short PEG spacer, a protease cleavable peptide (CP(AQ)) and a PEG masking tail.

The peptide backbone can be made of poly-lysine or poly-glutamate or any polymer that allows side-chain coupling. It contains a region for specific recognition by the TTU-CU linking domain on the TTU and it can be fluorescently labelled at one of its extremities. In the present example, the peptide backbone was made of poly-lysines and labelled with FITC. The short PEG spacer (Quanta Biodesign, Plain City, Ohio 43064) can be a PEG linker between the peptide backbone and the CP(AQ). The short PEG linker can be followed by different protease cleavable peptides carrying the antigen small molecule. In this example, the protease cleavable peptide is CP(AQ) (SEQ ID NO: 1). For comparison purposes, in this example, pCP(AQ) was also coupled to the short PEG linker. In the present example, CP(AQ) can also be linked to an Alexa fluor 647 (ThermoFisher Scientific, #A20347).

The PEG masking tail (Quanta Biodesign) can be of different length and complexities and it can be terminally bond to a fluorophore, different from the one on the peptide backbone to follow release of the masking PEG tail by the protease. In the present example, $PEG_{12}$ and $PEG_{24}$ with terminally bond Alexa fluor 647 (ThermoFisher Scientific, #A20347) can be coupled to CP(AQ).

Quantification of Tumor Target Binding by TTU

To quantify the ability of an TTU to target its cognate tumor antigen, a human $HER2^+$ cell line (HCC1954) was mixed with either TTU/AMH or AMH alone. Furthermore, a murine skin melanoma $HER2^-$ cell line was incubated with TTU/AMH to provide a negative control. In this example, it was used a Herceptin-base anti-HER2-TTU/AMH.

To test the TTU specificity, 100 000 HER2⁺ HCC1954 or HER2⁻ B16F10 cells were harvested with a cell scraper (MedSupply Partners #TL-TR9000). When necessary, the cells were incubated for 30 minutes on ice with 1 μg anti-HER2-TTU/AMH or 1 μg AMH in 100 μl PBS 2% FBS. After incubation, the cells were diluted with 400 μl PBS 2% FBS and centrifuged for 5 minutes at 500 g and 4° C. The supernatant was discarded and the cells were resuspended in 200 μl PBS 2% FBS. Finally, the cells were filtered through the cap of a Falcon FACS tube (Corning. #352235) and kept in a closed Styrofoam box with ice until analysis.

Validation of Tumor Target Binding by TTU/CU

To test the anti-HER2-TTU/CU binding, 100 000 HER2⁺ HCC1954 cells were harvested with a cell scraper (MedSupply Partners #TL-TR9000). The cells were stained with 0.4 μg of the same TTU module as previously, this time not linked to any fluorophore, and 0.4 μg of differently built CU modules (FIG. 10). All the CU here used have been labelled with FITC at their backbone. A second sample was also labelled with -PEG$_2$-pCP(AQ), a third with -PEG$_2$-CP(AQ)-A647, a fourth with -PEG$_2$-CP(AQ)-PEG$_{12}$-Alexa fluor 647 and finally one with -PEG$_2$-CP(AQ)-PEG$_{24}$-Alexa fluor 647. Both TTU and CU were added simultaneously to the cells. The cells were stained either 30 minutes on ice or for 8 hours at 37° C. and 5% CO$_2$.

After incubation at 37° C., the cells were scraped and the supernatant (500 μl) was transferred into an eppendorf tube. The cells were then diluted with 500 μl PBS 2% FBS and centrifuged for 5 minutes at 500 g and 4° C. The supernatant was discarded and the pellets were washed in 1000 μl PBS 2% FBS. Finally, the cells were resuspended in 200 μl PBS 2% FBS and filtered through the cap of a Falcon FACS tube (Corning, #352235). The cells were kept in a closed Styrofoam box with ice until analysis.

Results

Figure 11:
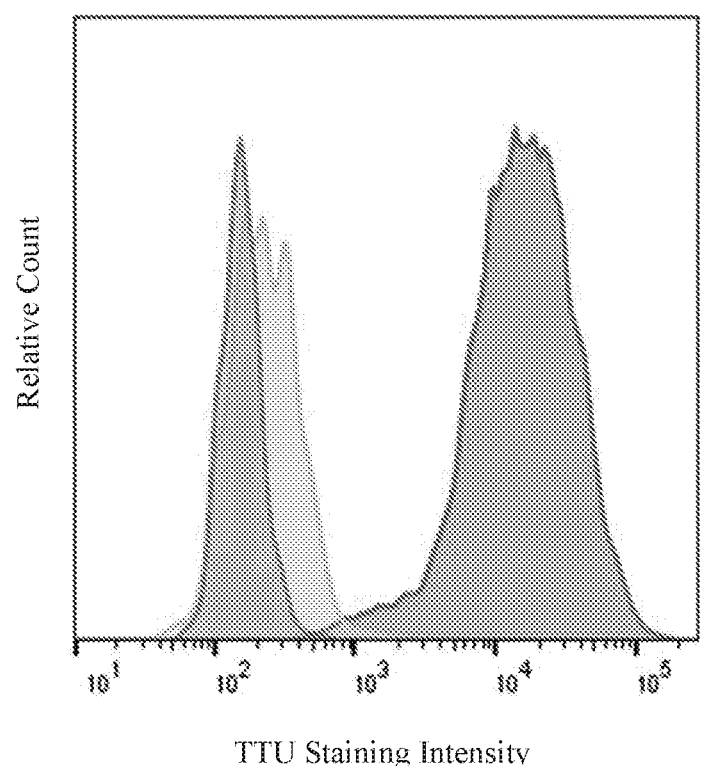
FIG. 11. HER2+ cell staining by Alexa fluor 647 labelled TTU. FACS analysis, Alexa fluor 647 signal as readout after 30 minutes incubation on ice.

The targeting specificity by TTU/AMH is shown in FIG. 11. The histogram of unstained HER2⁺ HCC1954 cells and the one of HER2⁻ B16F10 cells overlap, indicating that anti-HER2-TTU/AMH does not target off-site. As expected. HER2⁺ HCC1954 cells when incubated with the anti-HER2-TTU/AMH complex gives a strong Alexa fluor 647 signal.

Example of the data collected by FACS to verify the binding of a tumor target by the different a mixture of TTU-CU (Construct E in FIG. 10) is summarized in FIG. 12.

FIG. 12. Staining of HER2⁺ HCC1954 cells with anti-HER2-TTU and variable CU. Top. Data shown for HCC1954 cells stained with CU-FITC-CP(AQ)-PEG$_{24}$-Alexa fluor 647±TTU. The data collected show that the addition of TTU enhances the binding of the CU to the target tumor cell. Bottom. The data show the entire population of cells stained with CU-FITC-CP(AQ)-PEG$_{24}$-Alexa fluor 647+TTU after 30 minutes incubation on ice and 8 hours incubation at 37° C./5% CO$_2$. Since cells with the same FITC identity show a less intense A646 signal, the data collected prove that during a 8 hours incubation period there is minimal lysis of CP(AQ). FIG. 7, top, Target=HCC1954 cells, Effector=±TTU and CU-FITC-CP(AQ)-PEG$_{24}$-Alexa fluor 647.

Example 7: Construction of Anti-FITC Car T and its Components

Construct #1, encoding a polypeptide comprising "anti-FITC CAR T)

anti-FITC-4M5.3 antibody
(SEQ ID NO: 3)
DVVMTQTPLSLPVSLGDQASISCRSSQSLVHSNGNTYLRWYLQKPGQSPK
VLIYKVSNRVSGVPDRFSGSGSGTDFTLKINRVEAEDLGVYFCSQSTHVP
WTFGGGTKLEIKSSADDAKKDAAKKDDAKKDDAKKDGGVKLDETGGGLVQ
PGGAMKLSCVTSGFTFGHYWMNWVRQSPEKGLEWVAQFRNKPYNYETYYS
DSVKGRFTISRDDSKSSVYLQMNNLRVEDTGIYYCTGASYGMEYLGQGTS
VTVS Signal peptide-CD8a-sp|P01731|1-27-
(SEQ ID NO: 4)
MASPLTRFLSLNLLLLGESIILGSGEA Hinge region-CD8a-sp|P01731|152-194-
(SEQ ID NO: 5)
TTTKPVLRTPSPVHPTGTSQPQRPEDCRPRGSVKGTGLDFACD Transmembrane region (TM)-CD28-sp|P31041|151-177
(SEQ ID NO: 6)
FWALVVVAGVLFCYGLLVTVALCVIWT Intracellular domain (ICD)-CD28-sp|P31041|178-218
(SEQ ID NO: 7)
NSRRNRLLQSDYMNMTPRRPGLTRKPYQPYAPARDFAAYRP Intracellular domain (ICD)-41BB-sp|P20334|209-255
(SEQ ID NO: 8)
SVLKWIRKKFPHIFKQPFKKTTGAAQEEDACSCRCPQEEEGGGGGYEL Intracellular domain (ICD)-CD3z-sp|P24161|52-164
(SEQ ID NO: 9)
RAKFSRSAETAANLQDPNQLYNELNLGRREEYDVLEKKRARDPEMGGKQQ
RRRNPQEGVYNALQKDKMAEAYSEIGTKGERRRGKGHDGLYQGLSTATKD
TYDALHMQTLAPR anti-FITC CAR T-full peptide
(SEQ ID NO: 10)
MASPLTRFLSLNLLLLGESIILGSEGEADVVMTQTPLSLPVSLGDQASIS
CRSSQSLVHSNGNTYLRWYLQKPGQSPKVLIYKVSNRVSGVPDRFSGSGS
GTDFTLKINRVEAEDLGVYFCSQSTHVPWTFGGGTKLEIKSSADDSKKDA
AKKDDAKKDDAKKDGGVKLDETGGGLVQPGGAMKLSCVTSGFTFGHYWMN
WVRQSPEKGLEWVAQFRNKPYNYETYYSDSVKGRFTISRDDSKSSVYLQM
NNLRVEDTGIYYCTGASYGMEYLGQGTSVTVSTTTKPVLRTPSPVHPTGT
SQPQRPEDCRPRGSVKGTGLDFACDFWALVVVAGVLFCYGLLVTVALCVI
WTNSRRNRLLQSDYMNMTPRRPGLTRKPYQPYAPARDFAAYRPSVLKWIR
KKFPHIFKQPFKKTTGAAQEEDACSCRCPQEEEGGGGGYELRAKFSRSAE
TAANLQDPNQLYNENLGRREEYDVLEKKRARDPEMGGKQQRRRNPQEDVY
NALQKDKMAEAYSEIGTKGERRRGKGHDGLYQGLSTATKDTYDALHMQTL
APR**

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A binding molecule comprising:
   a binding domain having specificity for a tumor antigen, and
   a recognition domain, wherein the recognition domain comprises a small molecule less than about 5 kilodaltons in size,
   wherein the binding domain is covalently linked to the recognition domain, and wherein the binding domain is an antibody, an affimer, or a T-cell receptor (TCR) multimer,
   wherein the recognition domain is linked to a protection domain such that the recognition domain is masked,
   and wherein the protection domain comprises a protease susceptible peptide.

2. The binding molecule of claim 1, wherein the recognition domain specifically binds to a secondary binding molecule, and wherein the secondary binding molecule is on a cell, and wherein the cell is a chimeric antigen receptor T-cell (CAR T), a T-lymphocyte, a B-lymphocyte or natural Killer cell.

3. The binding molecule of claim 2, wherein the antibody is a Fab or a scFV; or wherein the TCR multimer is a tetramer.

4. The binding molecule of claim 1, wherein the protection domain comprises a carrier domain linked to a protease susceptible peptide; or
   wherein the protection domain comprises a masking peptide and a masking polymer; or
   wherein the protection domain is pH sensitive.

5. The protection domain of claim 4, wherein the masking polymer is PEG-diacrylate; or
   wherein the masking peptide comprises the amino acid sequence LysSerGlyProLeuGlyValArgGlySerSerCys (SED ID NO: 18); or
   wherein the masking peptide comprises a cleavable peptide.

6. The binding molecule of claim 4, wherein when the protection domain is contacted with a protease, the recognition domain is unmasked; and wherein when the protection domain is at a specific pH, the recognition domain is unmasked.

7. The binding molecule of claim 4, wherein the carrier domain is a polypeptide or a polymer; wherein the polymer is PEG-diacrylate.

8. The binding molecule of claim 6, wherein the protease susceptible peptide is specific for a tumor protease.

9. The binding molecule of claim 1, wherein the small molecule is:
   (a) synthetic or naturally-occurring;
   (b) biologically active or inactive;
   (c) a drug, a toxin, a hormone, a metal, a cytokine, a peptide or a nucleic acid;
   (d) fluorescein isothiocyanate (FITC), anthraquinone-2-acid, an amphetamine, a benzodiazepine, a benzoylecgonine, a buprenorphine, an opioid, a cannabinoid, a phencyclidine or a tricyclic antidepressant; or
   (e) dextromethorphan, fentanyl, meprobamate, methadone, methamphetamine, oxycodone, THC, tramadol, Zolpidem, ketamine, LSD, MDMA, methaqualone, propoxyphene or norketimine.

10. The binding molecule of claim 9, wherein the recognition domain comprises fluorescein isothiocyanate (FITC) or anthraquinone-2-acid.

11. The binding molecule of claim 1, wherein the binding domain is an antibody.

12. The binding molecule of claim 2, wherein the cell is a chimeric antigen receptor T-cell (CAR-T).

* * * * *

UNITED STATES PATENT AND TRADEMARK OFFICE
CERTIFICATE OF CORRECTION

| | |
|---|---|
| PATENT NO. | : 11,225,520 B2 |
| APPLICATION NO. | : 16/077939 |
| DATED | : January 18, 2022 |
| INVENTOR(S) | : Carl Novina et al. |

It is certified that error appears in the above-identified patent and that said Letters Patent is hereby corrected as shown below:

In the Claims

In Column 51, Line 31 in Claim 5:
Remove the following text:
"5. The protection domain of claim 4, wherein the masking"
And replace with the following text:
--5. The binding molecule of claim 4, wherein the masking--.

Signed and Sealed this
Twenty-fourth Day of May, 2022

Katherine Kelly Vidal
*Director of the United States Patent and Trademark Office*

SEQUENCE LISTING

<160> NUMBER OF SEQ ID NOS: 20

<210> SEQ ID NO 1
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: wherein lysine is covalently bound to
      anthraquinone-2-acid through its gamma amino group (AQ).

<400> SEQUENCE: 1

Lys Ser Gly Pro Leu Gly
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: wherein lysine is covalently bound to
      anthraquinone-2-acid through its gamma amino group (AQ).

<400> SEQUENCE: 2

Lys Ser Gly Pro Leu Gly Val Arg Gly Ser Ser Cys
1               5                   10

<210> SEQ ID NO 3
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 3

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Ser Ser Ala Asp Asp Ala Lys Lys Asp Ala Ala Lys Lys Asp Asp Ala
        115                 120                 125

Lys Lys Asp Asp Ala Lys Lys Asp Gly Val Lys Leu Asp Glu Thr
    130                 135                 140

Gly Gly Gly Leu Val Gln Pro Gly Gly Ala Met Lys Leu Ser Cys Val
145                 150                 155                 160

Thr Ser Gly Phe Thr Phe Gly His Tyr Trp Met Asn Trp Val Arg Gln

```
                165                 170                 175
Ser Pro Glu Lys Gly Leu Glu Trp Val Ala Gln Phe Arg Asn Lys Pro
            180                 185                 190

Tyr Asn Tyr Glu Thr Tyr Tyr Ser Asp Ser Val Lys Gly Arg Phe Thr
        195                 200                 205

Ile Ser Arg Asp Asp Ser Lys Ser Ser Val Tyr Leu Gln Met Asn Asn
    210                 215                 220

Leu Arg Val Glu Asp Thr Gly Ile Tyr Tyr Cys Thr Gly Ala Ser Tyr
225                 230                 235                 240

Gly Met Glu Tyr Leu Gly Gln Gly Thr Ser Val Thr Val Ser
                245                 250

<210> SEQ ID NO 4
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 4

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala
            20                  25

<210> SEQ ID NO 5
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 5

Thr Thr Thr Lys Pro Val Leu Arg Thr Pro Ser Pro Val His Pro Thr
1               5                   10                  15

Gly Thr Ser Gln Pro Gln Arg Pro Glu Asp Cys Arg Pro Arg Gly Ser
            20                  25                  30

Val Lys Gly Thr Gly Leu Asp Phe Ala Cys Asp
        35                  40

<210> SEQ ID NO 6
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 6

Phe Trp Ala Leu Val Val Val Ala Gly Val Leu Phe Cys Tyr Gly Leu
1               5                   10                  15

Leu Val Thr Val Ala Leu Cys Val Ile Trp Thr
            20                  25

<210> SEQ ID NO 7
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 7

Asn Ser Arg Arg Asn Arg Leu Leu Gln Ser Asp Tyr Met Asn Met Thr
```

-continued

```
                1               5                  10                 15
Pro Arg Arg Pro Gly Leu Thr Arg Lys Pro Tyr Gln Pro Tyr Ala Pro
                20                 25                 30

Ala Arg Asp Phe Ala Ala Tyr Arg Pro
            35                 40

<210> SEQ ID NO 8
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 8

Ser Val Leu Lys Trp Ile Arg Lys Phe Pro His Ile Phe Lys Gln
1               5                  10                 15

Pro Phe Lys Lys Thr Thr Gly Ala Ala Gln Glu Glu Asp Ala Cys Ser
                20                 25                 30

Cys Arg Cys Pro Gln Glu Glu Glu Gly Gly Gly Tyr Glu Leu
                35                 40                 45

<210> SEQ ID NO 9
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 9

Arg Ala Lys Phe Ser Arg Ser Ala Glu Thr Ala Ala Asn Leu Gln Asp
1               5                  10                 15

Pro Asn Gln Leu Tyr Asn Glu Leu Asn Leu Gly Arg Arg Glu Glu Tyr
                20                 25                 30

Asp Val Leu Glu Lys Lys Arg Ala Arg Asp Pro Glu Met Gly Gly Lys
                35                 40                 45

Gln Gln Arg Arg Arg Asn Pro Gln Glu Gly Val Tyr Asn Ala Leu Gln
            50                 55                 60

Lys Asp Lys Met Ala Glu Ala Tyr Ser Glu Ile Gly Thr Lys Gly Glu
65                  70                 75                 80

Arg Arg Arg Gly Lys Gly His Asp Gly Leu Tyr Gln Gly Leu Ser Thr
                85                 90                 95

Ala Thr Lys Asp Thr Tyr Asp Ala Leu His Met Gln Thr Leu Ala Pro
                100                105                110

Arg

<210> SEQ ID NO 10
<211> LENGTH: 553
<212> TYPE: PRT
<213> ORGANISM: Artificial Sequence
<220> FEATURE:
<223> OTHER INFORMATION: Synthetic polypeptide

<400> SEQUENCE: 10

Met Ala Ser Pro Leu Thr Arg Phe Leu Ser Leu Asn Leu Leu Leu
1               5                  10                 15

Gly Glu Ser Ile Ile Leu Gly Ser Gly Glu Ala Asp Val Val Met Thr
                20                 25                 30

Gln Thr Pro Leu Ser Leu Pro Val Ser Leu Gly Asp Gln Ala Ser Ile
                35                 40                 45
```

-continued

Ser Cys Arg Ser Ser Gln Ser Leu Val His Ser Asn Gly Asn Thr Tyr
    50                  55                  60

Leu Arg Trp Tyr Leu Gln Lys Pro Gly Gln Ser Pro Lys Val Leu Ile
 65                  70                  75                  80

Tyr Lys Val Ser Asn Arg Val Ser Gly Val Pro Asp Arg Phe Ser Gly
                 85                  90                  95

Ser Gly Ser Gly Thr Asp Phe Thr Leu Lys Ile Asn Arg Val Glu Ala
            100                 105                 110

Glu Asp Leu Gly Val Tyr Phe Cys Ser Gln Ser Thr His Val Pro Trp
        115                 120                 125

Thr Phe Gly Gly Gly Thr Lys Leu Glu Ile Lys Ser Ser Ala Asp Asp
    130                 135                 140

Ala Lys Lys Asp Ala Ala Lys Lys Asp Asp Ala Lys Lys Asp Asp Ala
145                 150                 155                 160

Lys Lys Asp Gly Gly Val Lys Leu Asp Glu Thr Gly Gly Gly Leu Val
                165                 170                 175

Gln Pro Gly Gly Ala Met Lys Leu Ser Cys Val Thr Ser Gly Phe Thr
            180                 185                 190

Phe Gly His Tyr Trp Met Asn Trp Val Arg Gln Ser Pro Glu Lys Gly
        195                 200                 205

Leu Glu Trp Val Ala Gln Phe Arg Asn Lys Pro Tyr Asn Tyr Glu Thr
    210                 215                 220

Tyr Tyr Ser Asp Ser Val Lys Gly Arg Phe Thr Ile Ser Arg Asp Asp
225                 230                 235                 240

Ser Lys Ser Ser Val Tyr Leu Gln Met Asn Asn Leu Arg Val Glu Asp
                245                 250                 255

Thr Gly Ile Tyr Tyr Cys Thr Gly Ala Ser Tyr Gly Met Glu Tyr Leu
            260                 265                 270

Gly Gln Gly Thr Ser Val Thr Val Ser Thr Thr Lys Pro Val Leu
        275                 280                 285

Arg Thr Pro Ser Pro Val His Pro Thr Gly Thr Ser Gln Pro Gln Arg
    290                 295                 300

Pro Glu Asp Cys Arg Pro Arg Gly Ser Val Lys Gly Thr Gly Leu Asp
305                 310                 315                 320

Phe Ala Cys Asp Phe Trp Ala Leu Val Val Ala Gly Val Leu Phe
                325                 330                 335

Cys Tyr Gly Leu Leu Val Thr Val Ala Leu Cys Val Ile Trp Thr Asn
            340                 345                 350

Ser Arg Arg Asn Arg Leu Leu Gln Ser Asp Tyr Met Asn Met Thr Pro
        355                 360                 365

Arg Arg Pro Gly Leu Thr Arg Lys Pro Tyr Gln Pro Tyr Ala Pro Ala
    370                 375                 380

Arg Asp Phe Ala Ala Tyr Arg Pro Ser Val Leu Lys Trp Ile Arg Lys
385                 390                 395                 400

Lys Phe Pro His Ile Phe Lys Gln Pro Phe Lys Lys Thr Thr Gly Ala
                405                 410                 415

Ala Gln Glu Glu Asp Ala Cys Ser Cys Arg Cys Pro Gln Glu Glu Glu
            420                 425                 430

Gly Gly Gly Gly Gly Tyr Glu Leu Arg Ala Lys Phe Ser Arg Ser Ala
        435                 440                 445

Glu Thr Ala Ala Asn Leu Gln Asp Pro Asn Gln Leu Tyr Asn Glu Leu
    450                 455                 460

Asn Leu Gly Arg Arg Glu Glu Tyr Asp Val Leu Glu Lys Lys Arg Ala

```
             465                 470                 475                 480

Arg Asp Pro Glu Met Gly Gly Lys Gln Gln Arg Arg Asn Pro Gln
                485                 490                 495

Glu Gly Val Tyr Asn Ala Leu Gln Lys Asp Lys Met Ala Glu Ala Tyr
            500                 505                 510

Ser Glu Ile Gly Thr Lys Gly Glu Arg Arg Gly Lys Gly His Asp
        515                 520                 525

Gly Leu Tyr Gln Gly Leu Ser Thr Ala Thr Lys Asp Thr Tyr Asp Ala
    530                 535                 540

Leu His Met Gln Thr Leu Ala Pro Arg
545                 550

<210> SEQ ID NO 11
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 11

Pro Leu Gly Val Arg Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 12

Pro Arg Cys Gly Val Pro Asp Val
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 13

Pro Arg Cys Gly Asn Pro Asp Val
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic polypeptide where "Val" can be
      substituted for any other amino acid

<400> SEQUENCE: 14

Pro Arg Cys Gly Val Pro Asp
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 15
```

Pro Arg Cys Gly Val Pro Asp Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 16

Pro Arg Cys Gly Val Pro Asp Lys
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 17

Gly Pro Ile Cys Phe Phe Arg Leu Gly Lys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 18

Lys Ser Gly Pro Leu Gly Val Arg Gly Ser Ser Cys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (12)..(12)
<223> OTHER INFORMATION: AMIDATION

<400> SEQUENCE: 19

Lys Ser Gly Pro Leu Gly Val Arg Gly Ser Ser Cys
1               5                   10

<210> SEQ ID NO 20
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 20

Pro Leu Gly Val Arg Gly
1               5